(12) United States Patent
Malek Tabrizi et al.

(10) Patent No.: US 10,363,174 B2
(45) Date of Patent: Jul. 30, 2019

(54) EYE TISSUE MEASUREMENTS

(71) Applicant: AMO DEVELOPMENT, LLC, Santa Ana, CA (US)

(72) Inventors: Alireza Malek Tabrizi, Fremont, CA (US); Harvey I. Liu, Fremont, CA (US); Hong Fu, Pleasanton, CA (US)

(73) Assignee: AMO DEVELOPMENT, LLC, Santa Ana, CA (US)

( * ) Notice: Subject to any disclaimer, the term of this patent is extended or adjusted under 35 U.S.C. 154(b) by 62 days.

(21) Appl. No.: 15/699,963

(22) Filed: Sep. 8, 2017

(65) Prior Publication Data

US 2018/0064577 A1 Mar. 8, 2018

Related U.S. Application Data

(60) Provisional application No. 62/385,167, filed on Sep. 8, 2016.

(51) Int. Cl.
*A61B 3/10* (2006.01)
*A61F 9/008* (2006.01)
*A61B 3/107* (2006.01)

(52) U.S. Cl.
CPC .......... *A61F 9/0084* (2013.01); *A61B 3/1005* (2013.01); *A61B 3/107* (2013.01); *A61B 3/1025* (2013.01); *A61F 9/008* (2013.01); *A61F 9/0081* (2013.01); *A61F 9/00814* (2013.01); *A61F 9/00836* (2013.01); *A61F 2009/00844* (2013.01); *A61F 2009/00872* (2013.01); *A61F 2009/00878* (2013.01); *A61F 2009/00897* (2013.01)

(58) Field of Classification Search
None
See application file for complete search history.

(56) References Cited

U.S. PATENT DOCUMENTS

| | | | |
|---|---|---|---|
| 2004/0102764 A1* | 5/2004 | Balling | A61F 9/008 606/5 |
| 2011/0251601 A1 | 10/2011 | Bissmann et al. | |
| 2015/0100012 A1 | 4/2015 | Muller | |
| 2015/0272782 A1 | 10/2015 | Schuele et al. | |
| 2015/0335477 A1 | 11/2015 | Schuele et al. | |

FOREIGN PATENT DOCUMENTS

| | | |
|---|---|---|
| WO | 0238323 A1 | 5/2002 |
| WO | 2014029407 A1 | 2/2014 |
| WO | 2014163891 A1 | 10/2014 |

OTHER PUBLICATIONS

International Search Report and Written Opinion for Application No. PCT/US20171050827, dated Dec. 12, 2017, 13 pages.

* cited by examiner

*Primary Examiner* — Ankit D Tejani
(74) *Attorney, Agent, or Firm* — Johnson & Johnson Surgical Vision, Inc.

(57) ABSTRACT

A compact system for performing laser ophthalmic surgery is disclosed. The systems and methods may be used to measure corneal thickness or other anatomy to prepare a treatment plan for any of numerous treatments, such as LASIK, PRK, intra stromal lenticular lens incisions, cornea replacement, or any other treatment. By using a reduced power femtosecond laser backscatter may be measured to calculate distances such as distances between an interior boundary and an exterior boundary of a cornea or other tissue.

20 Claims, 26 Drawing Sheets

110

| f_scan (Hz) | OPTP (deg) | OPTP (radian) | Mirror (mm×mm) | D (mm) | Mirror Material | Factor (1/mm) | f*OPTP*D (mm/s) | Duty Cycle β | 2θmax (deg) | α | 2400*cos(θπ/2)*f*OPTP*D (MHz) |
|---|---|---|---|---|---|---|---|---|---|---|---|
| 6000 | 20 | 0.349 | 7x8 | 7 | Glass | 2400 | 14661 | 0.66 | 17.2 | 86% | 17.9 |
| 8000 | 20 | 0.349 | 5x6 | 5 | Glass | 2400 | 13963 | 0.66 | 17.2 | 86% | 17.1 |
| 10000 | 16 | 0.279 | 4x5 | 4 | Glass | 2400 | 11170 | 0.66 | 13.8 | 86% | 13.6 |
| 12000 | 12 | 0.209 | 4x5 | 4 | Glass | 2400 | 10053 | 0.66 | 10.3 | 86% | 12.3 |
| 15000 | 8 | 0.140 | 4x5 | 4 | Glass | 2400 | 8378 | 0.66 | 6.9 | 86% | 10.2 |
| 6000 | 20 | 0.349 | 8x9 | 8 | Beryllium | 2400 | 16756 | 0.66 | 17.2 | 86% | |
| 8000 | 20 | 0.349 | 6x7 | 6 | Beryllium | 2400 | 16756 | 0.66 | 17.2 | 86% | |
| 10000 | 16 | 0.279 | 5x6 | 5 | Beryllium | 2400 | 13963 | 0.66 | 13.8 | 86% | 17.1 |
| 12000 | 12 | 0.209 | 5x6 | 5 | Beryllium | 2400 | 12566 | 0.66 | 10.3 | 86% | 16.4 |
| 15000 | 8 | 0.140 | 5x6 | 5 | Beryllium | 2400 | 10472 | 0.66 | 6.9 | 86% | 12.8 |
| 8000 | 26 | 0.454 | 6.5x7.8 | 4.7 | Beryllium | 2400 | 17062 | 0.66 | 22.4 | 86% | |

Figure 9

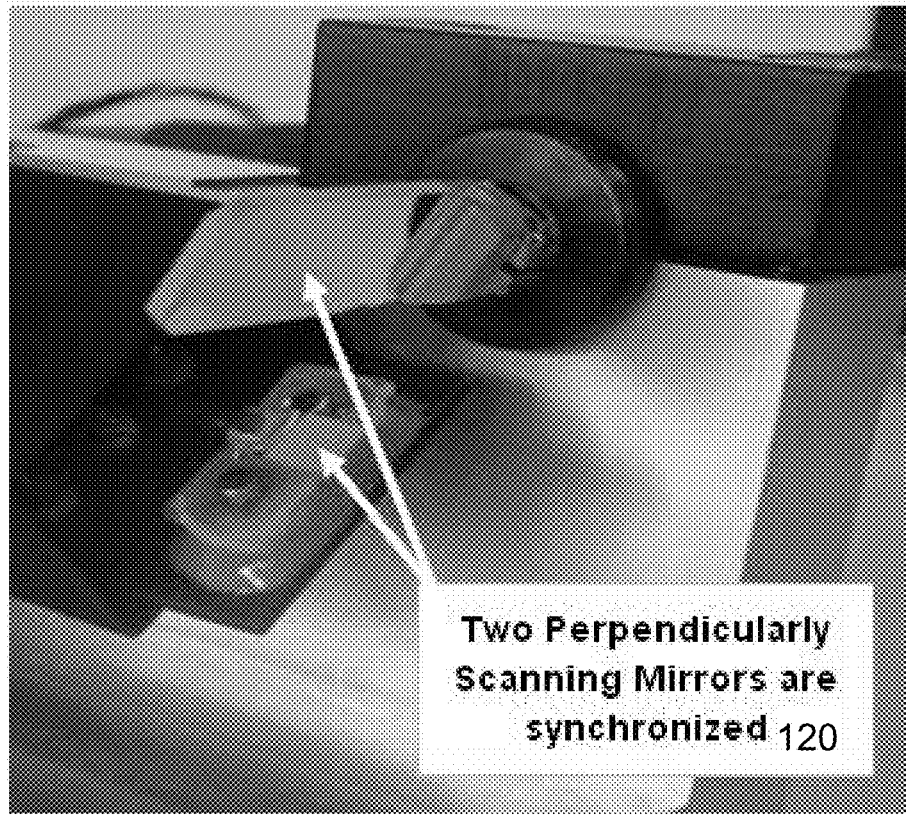
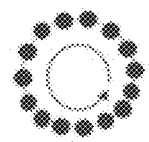
Figure 10

220

Calculate Visualization Beam Exit Heights

| | Parameter | Symbol | Formula | Value | Unit |
|---|---|---|---|---|---|
| 1 | Numerical Aperture | NA | Input | 0.800 | Dimensionless |
| 2 | Refractive Index | n | Input | 1.500 | Dimensionless |
| 3 | Cone Angle | α | α = arcsin(NA/n) | 33.578 | degree |
| 4 | Beam Splitting Surface Angle | β | Input | 24.000 | degree |
| 5 | Glass Height (Disposable+Spacer) | h1 | Input | 8.200 | mm |
| 6 | Radius of Field View | R | Input | 5.500 | mm |
| | Calculate Edge Ray Exit Height | | | | |
| 7 | Edge Ray Deviation Angle | γ | Input | 7.500 | degree |
| 8 | Auxiliary | AB | AB=h1/cos(α) | 9.847 | mm |
| 9 | Auxiliary | Angle AEB | Angle AEB=90-β-γ | 58.500 | degree |
| 10 | Auxiliary | BE | BE=AB*sin(α+γ)/sin(AEB) | 5.417 | mm |
| 11 | Edge Ray Exit Angle | θ2 | θ2 = 90-2β-γ | | degree |
| 12 | Auxiliary | Angle BEF | Angle BEF = 90+β+γ | 121.500 | degree |
| 13 | Auxiliary | BF | BF=BE*sin(BEF)/sin(θ2) | 8.154 | mm |
| 14 | Auxiliary | BP | BP=2*R+2*h1*tan(α) | 18.158 | mm |
| 15 | Auxiliary | FP | FP=BP-BF | 10.004 | mm |
| 16 | Auxiliary | Angle FKP | Angle FKP=2β+γ-α | 31.922 | degree |
| 17 | Auxiliary | FK | FK=FP*sin(90+α)/sin(FKP) | 17.339 | mm |
| 18 | Height of Exit Point for Edge Ray | h3 | h3=FK*sin(θ2) | | mm |
| | Calculate Center Ray Exit Height | | | | |
| 19 | Auxiliary | BQ | BQ=BP/2 | 9.079 | mm |
| 20 | Auxiliary | GQ | GQ=BQ*tan(β) | 4.042 | mm |
| 21 | Center Ray Exit Angle | θ4 | θ4=90-2β | | degree |
| 22 | Auxiliary | HQ | HQ=GQ/tan(θ4) | 4.468 | mm |
| 23 | Auxiliary | HP | HP=PQ-HQ | 4.590 | mm |
| 24 | Auxiliary | Angle HJP | Angle HJP=2β-α | 24.422 | degree |
| 25 | Auxiliary | HJ | HJ=HP*sin(90+α)/sin(HJP) | 10.174 | mm |
| 26 | Height of Exit Point for Center Ray | h2 | h2=HJ*sin(90-2β) | | mm |
| | Calculate Beam Splitter Height | | | | |
| 27 | Auxiliary | Angle BSP | Angle BSP=90-α-β | 42.422 | degree |
| 28 | Auxiliary | BS | BS=BF*sin(90+α)/sin(BSP) | 24.676 | mm |
| 29 | Height of Beam Splitter | h4 | h4=BS*sin(β) | | mm |

Figure 15

EYE TISSUE MEASUREMENTS

CROSS-REFERENCES TO RELATED APPLICATIONS

This application claims priority to, and the benefit of, under 35 U.S.C. § 119(e) of U.S. Provisional Appl. No. 62/385,167, filed Sep. 8, 2016, which is incorporated herein by reference in its entirety.

TECHNICAL FIELD

Embodiments of this invention generally relate to the field of eye surgery, and more specifically to eye tissue measurements using an ophthalmic laser system.

BACKGROUND

Vision impairments such as myopia (near sightedness), hyperopia (far sightedness), and astigmatism can be corrected using eyeglasses or contact lenses. Alternatively, the cornea of the eye can be reshaped surgically to provide the needed optical correction.

Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures. The reason eye surgeons prefer a surgical laser beam over manual tools like microkeratomes and forceps is that the laser beam can be focused precisely on extremely small amounts of ocular tissue, thereby enhancing accuracy and reliability of the procedure. These in turn enable better wound healing and recovery following surgery.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm. Examples of laser systems that provide ultra-short pulsed laser beams include the Abbott Medical Optics iFS Advanced Femtosecond Laser, the IntraLase FS Laser, and OptiMedica's Catalys Precision Laser System.

Current surgical approaches for reshaping the cornea include laser assisted in situ keratomileusis (hereinafter "LASIK"), photorefractive keratectomy (hereinafter "PRK") and Small Incision Lens Extraction (hereinafter "SMILE").

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like.

Traditionally, to measure various tissues within an eye to determine a treatment plan, surgeons would measure the thickness of an eye tissue, such as a cornea by manually placing an ultrasound device on the eye in different places, manually. This methodology can be cumbersome. Hence, there is a need for improved systems and methods of measuring eye tissues without resorting to manual methods.

SUMMARY

Hence, to obviate one or more problems due to limitations and disadvantages of the related art, this disclosure provides systems and methods for use in suitable ophthalmic laser surgery systems. Embodiments as described herein provide improved methods and apparatus to facilitate ophthalmic surgical procedures for the eye.

Embodiments of Methods and systems described here include measuring corneal thickness, including generating a femtosecond pulsed laser beam of less than 40 milliwatts in power, directing the laser beam into the cornea of an eye of a patient, the cornea having an interior side toward a center of the eye and an exterior side, focusing the directed laser beam to a focus point beyond the cornea interior into the eye, moving the focus point of the laser beam through the cornea toward the exterior side of the cornea, moving the focus point of the laser beam past the exterior side of the cornea, receiving a backscatter of the laser beam as the focus point moves, determining a time corresponding to the received backscatter of the laser beam as the focus point moves, calculating a distance between the cornea interior and cornea exterior based on the received backscatter and corresponding time as the focus point moves.

Embodiments of the invention include the laser beam having a wavelength between 300 nm and 1200 nm. Embodiments may also include the laser having a wavelength between 1020 and 1040 nm. Embodiments may further include the laser beam having a numerical aperture NA between 0.3 and 1.3.

Embodiments of the invention include a polarized laser beam. Embodiments may include the laser beam having a pulsed laser beam having a pulse duration between 10 femtoseconds and 10 picoseconds.

Systems and methods here include docking a femtosecond laser patient interface to a cornea of a patient, attenuating the femtosecond laser power to a level for measuring, wherein the attenuated femtosecond laser has a power at the focus point of less than 40 milliwatts, focusing the femtosecond laser to a beam at a focal point in the interior side of the cornea of the patient in x lateral axis, y lateral axis and a z depth axis, moving the femtosecond laser focal point in the z axis from the interior side of the cornea through the cornea and toward an exterior side of the cornea, capturing a backscatter of the femtosecond laser focal point as it moves in the z axis from the interior side of the cornea to the exterior side of the cornea, and recording a time the femtosecond laser focal point moves in the z depth axis from the interior side of the cornea to the exterior side of the cornea, calculating a power of the captured backscatter as the laser focal point moves in the z depth axis from the interior side of the cornea to the exterior side of the cornea, determining a cutting distance, based on the recorded time the laser focal point moves and the calculated power of the captured backscatter, powering up the femtosecond laser from the measuring power to an incision power, incising the cornea at the determined cutting distance in the cornea to remove a portion of the cornea. Alternatively or additionally, the cutting distance is 50 μm from an endothelium layer of the cornea. Alternatively or additionally, the systems and methods may include determining, from the captured backscatter, a folded shape of the cornea while the patient interface is docked, wherein the incision on the cornea at the determined cutting distance follows the folded shape of the docked cornea. Alternatively or additionally, the incision following the folded shape of the cornea while docked does not incise an endothelium layer in the cornea. Alternatively or additionally, the laser has a wavelength between 1020 nm and 1040 nm. Alternatively or additionally, the laser has a wavelength between 335 nm and 400 nm. Alternatively or additionally, wherein the laser beam has a numerical aperture NA between 0.3 and 1.3. Alternatively or additionally, the laser beam is polarized. Alternatively or additionally, the laser beam is a pulsed laser beam having a pulse duration between 10 femtoseconds and 10 picoseconds.

This summary and the following detailed description are merely exemplary, illustrative, and explanatory, and are not intended to limit, but to provide further explanation of the embodiments as claimed. Additional features and advantages of the embodiments will be set forth in the descriptions that follow, and in part will be apparent from the description, or may be learned by practice of the embodiments. The objectives and other advantages of the embodiments will be realized and attained by the structure particularly pointed out in the written description, claims and the appended drawings.

BRIEF DESCRIPTION OF THE DRAWINGS

The novel features of the embodiments are set forth with particularity in the appended claims. A better understanding of the features and advantages will be facilitated by referring to the following detailed description that sets forth illustrative embodiments using principles of the embodiments, as well as to the accompanying drawings, in which like numerals refer to like parts throughout the different views. Like parts, however, do not always have like reference numerals. Further, the drawings are not drawn to scale, and emphasis has instead been placed on illustrating the principles of the embodiments. All illustrations are intended to convey concepts, where relative sizes, shapes, and other detailed attributes may be illustrated schematically rather than depicted literally or precisely.

FIG. 9 is a table of scanner parameters according to certain embodiments.

FIG. 10 illustrates a perspective view of a scanner system according to certain embodiments.

FIG. 15 illustrates a table of visualization parameters according to certain embodiments.

DETAILED DESCRIPTION

Embodiments of this invention are generally directed to systems and methods for laser-assisted ophthalmic procedures.

Figure 1A:
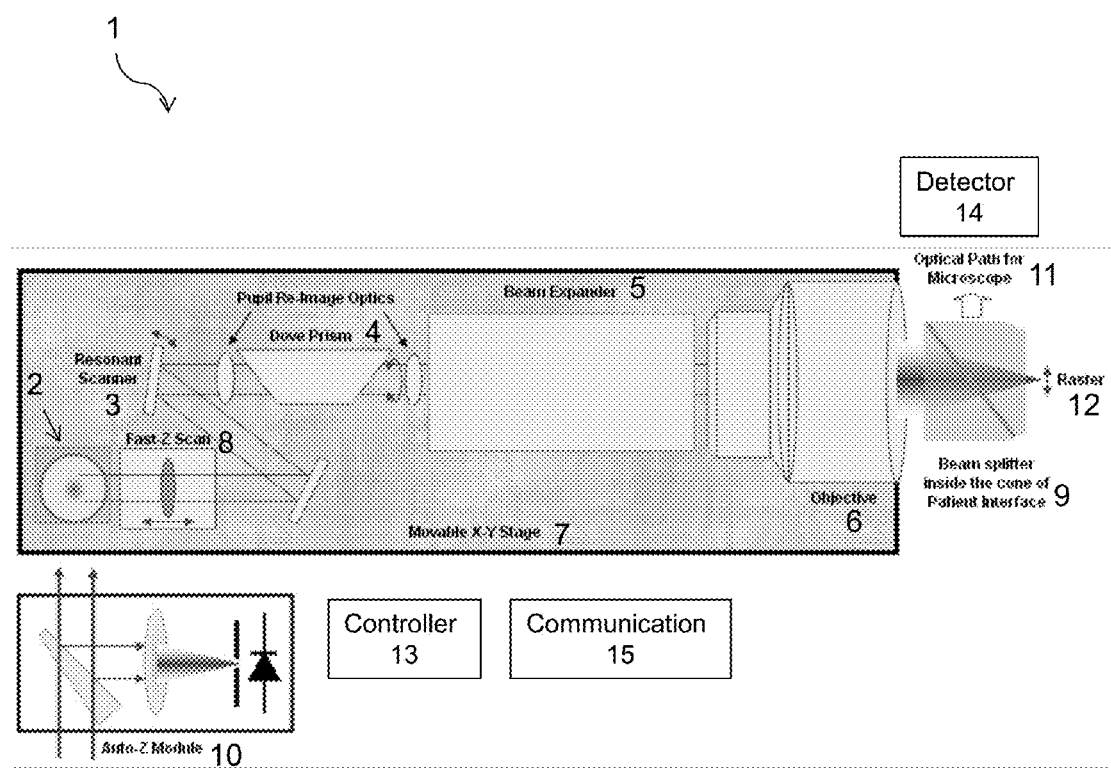
FIGS. 1A and 1B are simplified diagram views of a surgical ophthalmic laser system according to certain embodiments.

Referring to the drawings, FIG. 1A shows an ophthalmic surgical laser system 1 for making an incision in a target material such as a cornea of an eye. A laser 2 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. The laser may be a micro-chip picosecond laser. For example, a laser beam delivery system may be used to scan the pulsed laser beam to produce an incision in the material, create a flap of material, create a pocket within the material, form removable structures of the material, and the like. The term "scan" or "scanning" refers to the movement of the focal point of the pulsed laser beam along a desired path or in a desired pattern.

Although the laser system 1 may be used to photoalter a variety of materials (e.g., organic, inorganic, or a combination thereof), the laser system 1 is suitable for ophthalmic applications. For example, the focusing optics direct the pulsed laser beam toward an eye (for example, onto or into a cornea) for plasma mediated (for example, non-UV) photoablation of superficial tissue, or into the stroma of the cornea for intrastromal photodisruption of tissue.

The system 1 includes, but is not limited to, a laser source 2 capable of generating a pulsed laser beam, a resonant scanner 3 for producing a fast scan line or raster 12 of the pulsed laser beam, an XY scan device 4 or scan line rotator (e.g., a Dove prism, Pechan prism, or the like) for rotating the scan line 12, a beam expander 5, an objective 6, a moveable XY stage 7 for deflecting or directing the pulsed laser beam from the laser 1 on or within the target, a fast-Z scan device 8, a patient interface 9 that may include a visualization beam splitter inside a cone, an auto-Z device 10 for modifying the depth of the pulse laser beam and providing a depth reference, an optical path 11, a controller 13, and a communication module 15. An imaging video camera may further be included.

The laser beam delivery system of the system 1 delivers a pulsed laser beam at a focal point of a target in a patient's eye in a raster pattern and may include the resonant scanner 3, beam expander 5, objective 6 and patient interface 9.

The focal point of the target in the patient's eye may include one or more of a cornea, stroma, capsular bag, crystalline lens, and zonule. The pulsed laser beam may modify the target in the patient's eye to produce corneal tissue modification such as corneal cross-linking. As a result of the pulsed laser beam, a desired incision may be produced in the patient's eye.

The resonant scanner 3 generates a fast scan line at a fixed resonant frequency. The resonant scanner 3 may produce a raster between 1 mm and 2 mm where a width of the scan line may be adjusted. A resonant scanner scans very fast and produces a one-dimensional scan that is, for example, a horizontal line.

The XY scan device 4 or scan line rotator moves the pulsed laser beam raster 12 in a lateral direction so as to rotate the scan line to any desired orientation on an XY plane. For example, a Dove prism or Pechan prism rotates the raster to any direction on an XY plane such as a scan line perpendicular to the XY device 7 trajectory to provide scan coverage over a larger area.

The XY scan device 7 is a movable XY scanning stage having a final focusing objective 6 mounted thereon. The XY scan device 7 carries the final objective 6 to move the fast scan line to cover an entire treatment area. The movable XY scanning stage 7 may include a recoilless stage configured to reduce or eliminate mechanical vibration. The XY scanning stage 7 is configured to move the pulsed laser beam in a lateral direction such that the laser beam may cover an entire surgical field of the patient's eye. Accordingly, the scan line rotator 4 modifies an orientation of the scan line while the moveable XY scanning stage moves the optical field of the scan line across an XY plane.

The fast Z scan device 8 modifies a depth of focus of the pulsed laser beam and may provide fine depth control. The fast Z scan device 8 may either be set at a fixed position or run dynamically to correct the system's inherent depth variations at different (X,Y) locations. In the latter case, a fast Z position is determined by the XY trajectory and does not affect the XY trajectory. A fast Z scan sets a cut depth and moves the focus in the depth direction to produce, for example, a side-cut in a target material.

A shutter (not shown) can be kept open during a bed cut or may be controlled to open/close to block the unwanted pulses during a bed cut.

The patient interface 9 couples the patient's eye to the ophthalmic surgical laser system 1. The patient interface design has a fixed cone nose on the system. The disposable part of the patient interface is single-piece device that allows the use of flat applanation, or the use of liquid interface, for patient sitting upright, respectively. Any design with a separated suction ring does not apply for a patient sitting upright. The patient interface 9 may include a visualization beam splitter in the cone of the patient interface. A beam splitter is placed inside this cone to allow the full eye to be imaged via visualization optics. This allows the system to be made smaller. The patient interface may be removed when an eye-tracking system is used. Visualization may be provided through, for example, a video microscope or ocular microscope.

The auto Z module 10 measures a distal end surface of a lens cone of the patient interface coupled to the patient's eye and provides a depth reference for the Z scan device 8 of the ophthalmic laser system. The auto Z module 10 uses the focus of a surgical beam as the measurement probe, so there is no need to calibrate the measurement reference and the laser focus, which is otherwise required for other depth measurement methods, such as optical coherence tomography (OCT).

The controller 13 is operably coupled with the laser delivery system, the XY scan device 4, the Z scan device 8, detector 14 and the communication module 15. The controller 13 is configured to direct the laser delivery system to output the pulsed laser beam in a desired pattern at the focal point of the target in the eye so as to modify the target.

The controller 13, such as a processor operating suitable control software, is operatively coupled with the components of the system 1 to direct a fast scan line 12 of the pulsed laser beam along a scan pattern on or in the target material.

In some embodiments, the system 1 includes a beam splitter within the patient interface 9 and a detector 14 coupled to the controller 13 for closed-loop feedback control mechanism (not shown) of the pulsed laser beam. Other feedback methods may also be used, including but not necessarily limited to position encoder on the scanner 3 or the like.

In one embodiment, the pattern of pulses may be summarized in machine-readable data of tangible storage media in the form of a treatment table. The treatment table may be adjusted according to feedback input into the controller 13 from an automated image analysis system in response to feedback data provided from an ablation monitoring system feedback system (not shown). Optionally, the feedback may be manually entered into the controller 13 by a system operator.

The feedback may also be provided by integrating a wavefront measurement system (not shown) with the laser surgery system 1. The controller 13 may continue and/or terminate at least one incision in response to the feedback, and may also modify the planned sculpting based at least in part on the feedback. Measurement systems are further described in U.S. Pat. No. 6,315,413, the entire disclosure of which is incorporated herein by reference.

The communication module 15 provides information to the operator of the laser system 1 at the system and/or remotely via wired or wireless data connection. The communication module 15 may include a display device and input/output devices as known in the art to display information to an operator. An operator may control the system 1 via any known input control system including but not limited to a keyboard, a mouse, voice control, a motion sensing system, a joystick, and an eye-tracking system. The system 1 may be operated remotely and may also be monitored and serviced remotely.

Figure 1B:
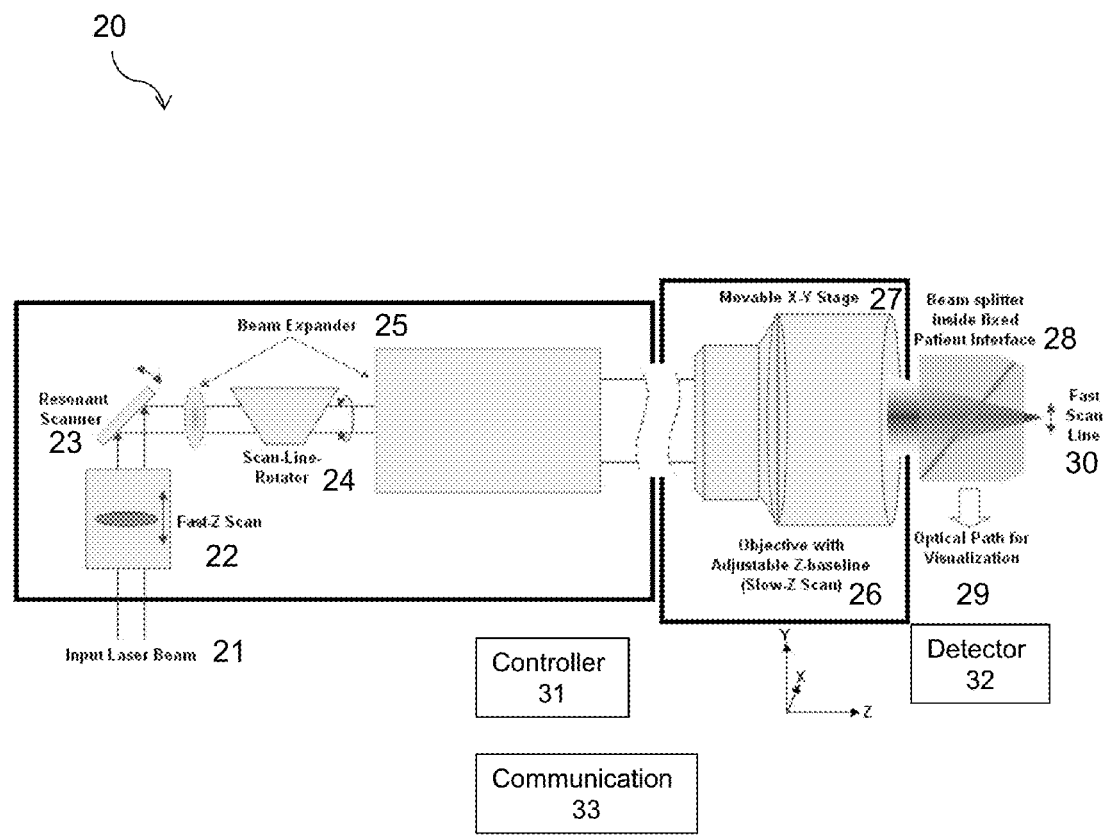

In another embodiment, FIG. 1B shows the beam delivery optics of a system 20. The system 20 includes, but is not limited to, an input pulsed laser beam 21 from laser source (not shown), fast-Z scan 22, a resonant scanner 23 for producing a fast scan line 30 of the pulsed laser beam 21, a scan line rotator 24 (e.g., a Dove or Pechan prism, or the like) for rotating the scan line 30, a beam expander 25, an objective 26 with an adjustable Z-baseline (slow-Z scan) 26, a moveable X-Y stage 27 for deflecting or directing the pulsed laser beam 21 on or within the target, a patient interface 28 that may include a beam splitter, an optical path 29, a controller 31, a detector 32, and a communication module 33. The slow-Z scan 26 sets the focus at a fixed depth and may set the Z-baseline. For example, the slow-Z scan 26 is stationary during a bed cut.

Some embodiments of the system are compact desktop systems that are placed on a table or the like. Other embodiments may include a motorized stage. The compact system allows a patient and patient interface to be oriented downwards, upwards, or in any direction, and not necessarily upright.

Figure 2A:
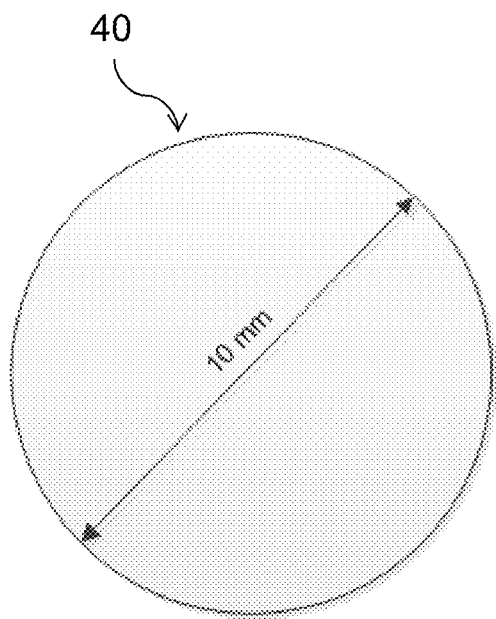
FIGS. 2A and 2B are simplified views of an optical field according to certain embodiments.

Next, FIG. 2A provides a simplified view of a surgical field 40. Typically, laser-assisted ophthalmic procedures are performed within a surgical field 40 of an eye that has a diameter of about 10 mm. Some of these systems utilize solid state femtosecond lasers including an oscillator, stretcher, amplifier and compressor. Conventional laser systems include a laser with optics large enough to generate a laser beam with an optical field that matches the surgical field. Scanning mirrors or other optics (not shown) may be provided to angularly deflect and scan the pulsed laser beam over the entire surgical field. These scanning mirrors may be driven by a set of galvanometers that further add to the bulk and complexity of conventional laser systems.

However, providing a sufficient numerical aperture (NA) to perform laser surgery requires large, expensive optics and a corresponding cumbersome, heavy and expensive beam delivery system. For example, an objective of the iFS Advanced Femtosecond Laser System alone weighs over 30 lbs. in order to allow a pulsed laser beam to scan freely within the 10 mm surgical field. These systems provide a practical maximum NA of about 0.4 due to the increasing cost, size and complexity of system components when NA is increased.

Figure 2B:
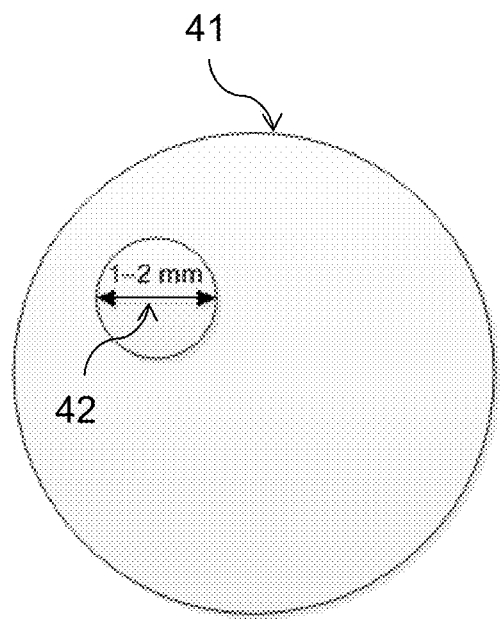

FIG. 2B illustrates an optical field 42 according an embodiment of the embodiments that are significantly smaller in diameter than the surgical field 41. The diameter of the optical field 42 depends on the length of the fast scan line 12 generated by the resonant scanner 3. For example, the diameter of the optical field 42 may be between 1 mm and 2 mm, and may preferably be 1.2 mm. This allows the laser to be made much smaller with laser beam tissue interaction in a low-density plasma mode.

For a given NA, the size and cost of the laser optics is reduced as the optical field is reduced in size. Consequently, increasing an NA value is significantly more cost effective for a smaller optical field. Since the optical field 42 may be about five to ten times smaller than the surgical field 41, a higher NA is achievable at a reduced cost compared to an optical field matching the surgical field 40. Accordingly, the embodiments provides higher NA at lower cost.

As shown in FIG. 2B, an optical field 42 does not by itself cover an entire surgical field 41. However, the optical field 42 is moved mechanically by the moveable XY device 7 across the entire surgical field 41. As will be described later, a resonant scanner 3 generates a very fast scan line within the optical field 42 that is oriented (rotated) within the optical field 42 by an XY scan device 4 and moved within the entire surgical field 41 by the moveable XY scan device 7. Reducing the size of the optical field significantly reduces the complexity, size, and weight of the laser source. Furthermore, an opto-mechanic arm mechanism is unnecessary in the laser system 1. In this manner, the laser optics are provided at a much lower cost with improved focus to achieve better surgical outcomes.

Embodiments of the embodiments may utilize a femtosecond oscillator or oscillator low energy laser. The laser source 2 may include an active medium fiber laser amplifier, oscillator and compressor, but need not include a stretcher. The laser source 2 may be fiber oscillator based, such as a diode-pumped fiber laser. The diode-pumped fiber laser may be a mode-locked fiber oscillator based laser having a single-mode, double-clad fiber oscillator and all positive dispersion elements.

The laser may generate a pulsed laser beam having a pulse repetition rate in the range between 5 MHz and 40 MHz, pulse energy in the range between 1 nJ and 5 µJ, a wavelength between the range of 1020 nm and 1065 nm, a pulse duration between the range of 10 femtoseconds and 10 picoseconds, a spot size between 0.2 µm and 2.0 µm (FWHM), and a numerical aperture NA between 0.25 and 1.3. An NA of 0.6 produces a 1.1 µm FWHM spot. The NA value is preferably provided between 0.25 and 1.0, more preferably between 0.4 and 1.0, and may be 0.6 in the illustrated examples.

Moreover, the reduction in size and complexity of the system 1 allows the laser delivery system to be configured to deliver the pulsed laser beam to the focal point of the target in the patient's eye while the patient is seated either in an upright position or in a reclining position.

Figure 3:
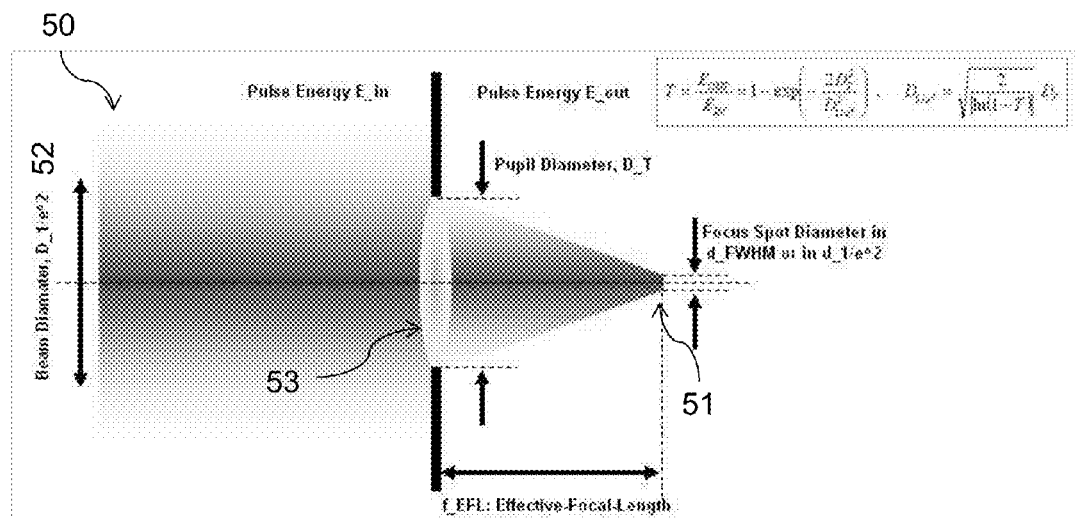
FIG. 3 is a diagram of a pulsed laser beam according to certain embodiments.

FIG. 3 is a diagram of a pulsed laser beam 50 including the relationship between the beam diameter, pulse energies, focus spot diameters and effective focal length. The focus spot 51 generated by a laser 2 may be provided at a focus point of the cornea to generate a bubble that separates and dissects tissue.

A pulsed laser beam directed at corneal tissue will first generate plasma. Additional pulses then generates a bubble in tissue. Finally, the bubble expands to generate tissue separation/dissection.

A pulsed laser beam applied to tissue first generates plasma, which then generates a bubble, and finally leads to tissue separation/dissection. A typical threshold value for tissue dissection is $10^{13}$ W/cm$^2$. To perform tissue dissection, a pulsed laser beam needs to reach or exceed this threshold value determined by the equation $\epsilon/\tau\sigma$, where $\epsilon$ is the energy of the beam, $\tau$ is the pulse width, and $\sigma$ is the area of the beam.

Based on this relationship, for a given amount of energy, decreasing the spot size will increase the optical density of the beam since the same amount of beam energy is concentrated in a smaller area. Likewise, as the spot size of the beam decreases, the amount of energy of the beam may be reduced while still exceeding the tissue dissection threshold value. A smaller amount of beam energy applied in a smaller area results in a finer tissue cut.

An inverse relationship exists between spot size and numerical aperture such that as NA becomes larger, a spot size 51 becomes smaller. Numerical aperture represents the sine of the half angle of the cone of a laser beam. Accordingly, a higher NA value is desirable in providing a finer cut.

For example, the laser system 1 outputs an energy level of 0.14 µJ that is 20% of the energy level output of 0.7 µJ from the iFS Laser System. Similarly, the system 1 provides a pulse width of 120 fs and area of $\pi \cdot 0.5^2$ µm$^2$ while the iFS Laser System provides a pulse width of 600 fs and area of $\pi \cdot 0.8^2$ µm$^2$.

Figure 4:
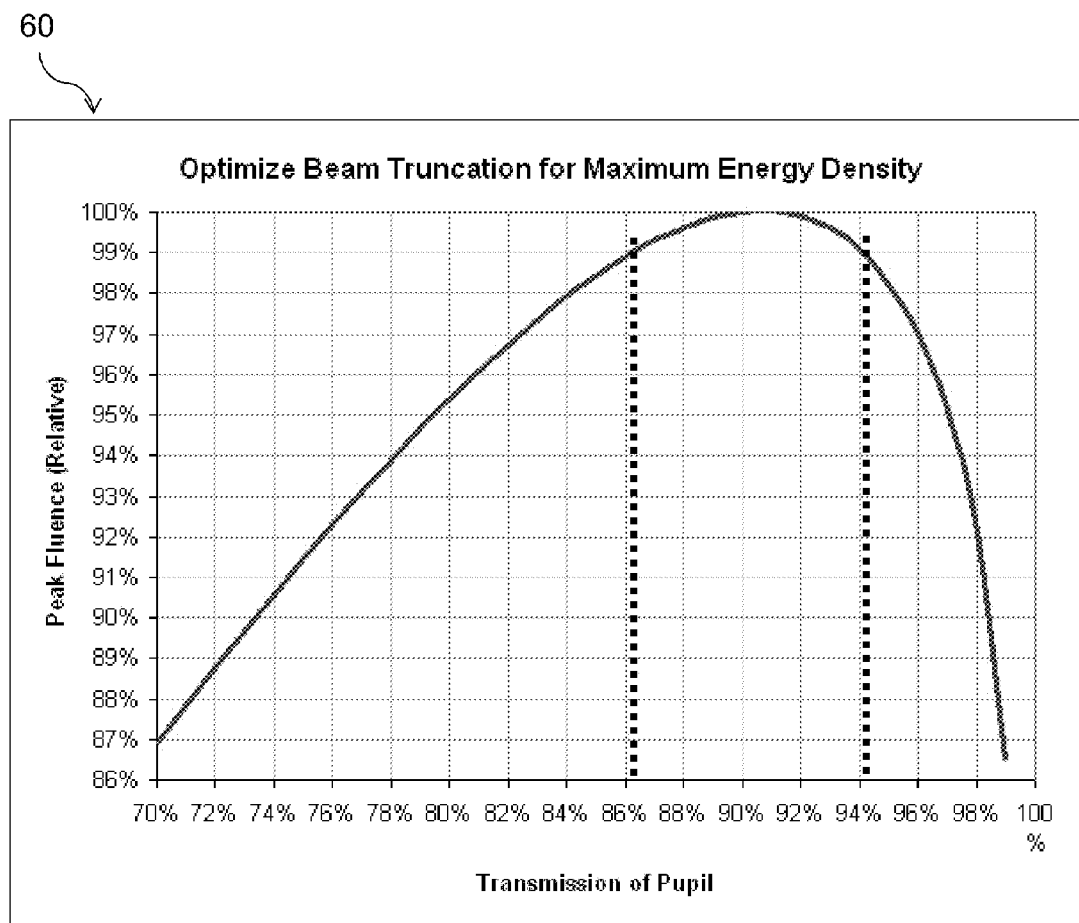
FIG. 4 is a graph related to laser beam optimization according to certain embodiments.

FIG. 4 is a graph 60 related to laser beam optimization. As illustrated in FIG. 3, a beam diameter 52 may be different from the diameter of a lens 53 that focuses the light pulse into a focus spot 51. Selection of a beam diameter 52 smaller than the lens diameter 53 ensures that all of the light energy passes through the lens. However, an inverse relationship exists between a beam diameter and a focus spot size such that the focus spot size will increase as the beam diameter decreases. $F_{PEAK}$ represents energy area density and T represents energy transmission.

Similarly, laser overfield is a configuration where the beam diameter 52 is greater than the lens diameter 53 such that a portion of the light energy is not transmitted through the lens and lost. But, the loss in energy efficiency by laser overfield provides the benefit of a smaller focus spot size 51.

In balancing the factors of energy efficiency and spot size, FIG. 4 illustrates the optimal conditions to attain maximum energy density. In particular, a maximum peak fluence is achieved with about a 10% loss of transmission. In other words, the optimum ratio of energy transmission to spot size occurs when the pulsed laser beam diameter is about 10% larger than the lens diameter.

A laser as described above may operate at very high frequencies such as on the order of 10 MHz (or 10,000,000 pulses/sec). Laser pulses that are not scanned will be directed at a single point which is unsuitable for ophthalmic procedures. Therefore, a scanner is needed to operate at a sufficient frequency to scan these pulses across a surgical area.

The scanner 3 of the system 1 may be a high frequency resonant optical scanner having a fixed frequency in a range between 3500 Hz and 21,000 Hz. In an preferred embodiment, a 7910 Hz resonant scanner is implemented. Use of a resonant scanner is particularly effective as they have no wearing parts, are reliable, cost-effective and compact (e.g., 1.0"W×0.7"D×2.5"H). The resonant scanner 3 produces a line raster pattern with a length of the raster pattern between 0.5 mm and 2 mm. In some embodiments, the resonant optical scanner is configured to scan the pulsed laser beam from the laser delivery system in a line.

Figure 5:
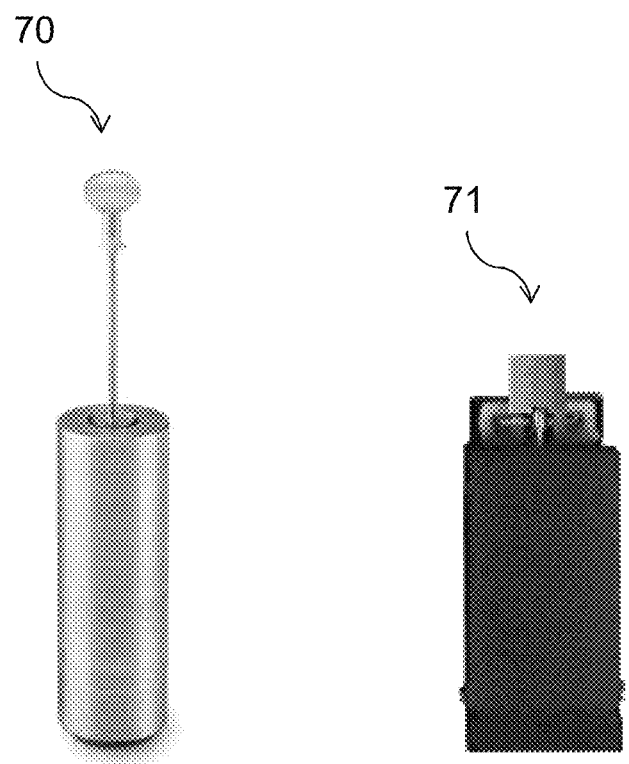
FIG. 5 illustrates resonant scanners according to certain embodiments.

FIG. 5 illustrates exemplary resonant scanners 70 and 71 that include a mirror attached to a metal rod that vibrates at an inherent resonant frequency. The shape and composition of the rod are selected to operate at a desired frequency to scan laser pulses. The resonant scanner 3 does not require a plurality of mirrors or a set of cumbersome galvos to scan across a surgical field as other systems do. Instead, the scan line may be rotated by a scan line rotator within an optical field and the scanner 3 may be scanned across a surgical field by a moveable XY stage. In some embodiments, the resonant scanner 3 provides an order of magnitude in weight and cost savings over the scanner system provided in the iFS Laser System. The resonant scanner 3 may scan at a rate of about 20 m/s while the iFS scanner scans at a rate of about 3 m/s.

Figure 6:
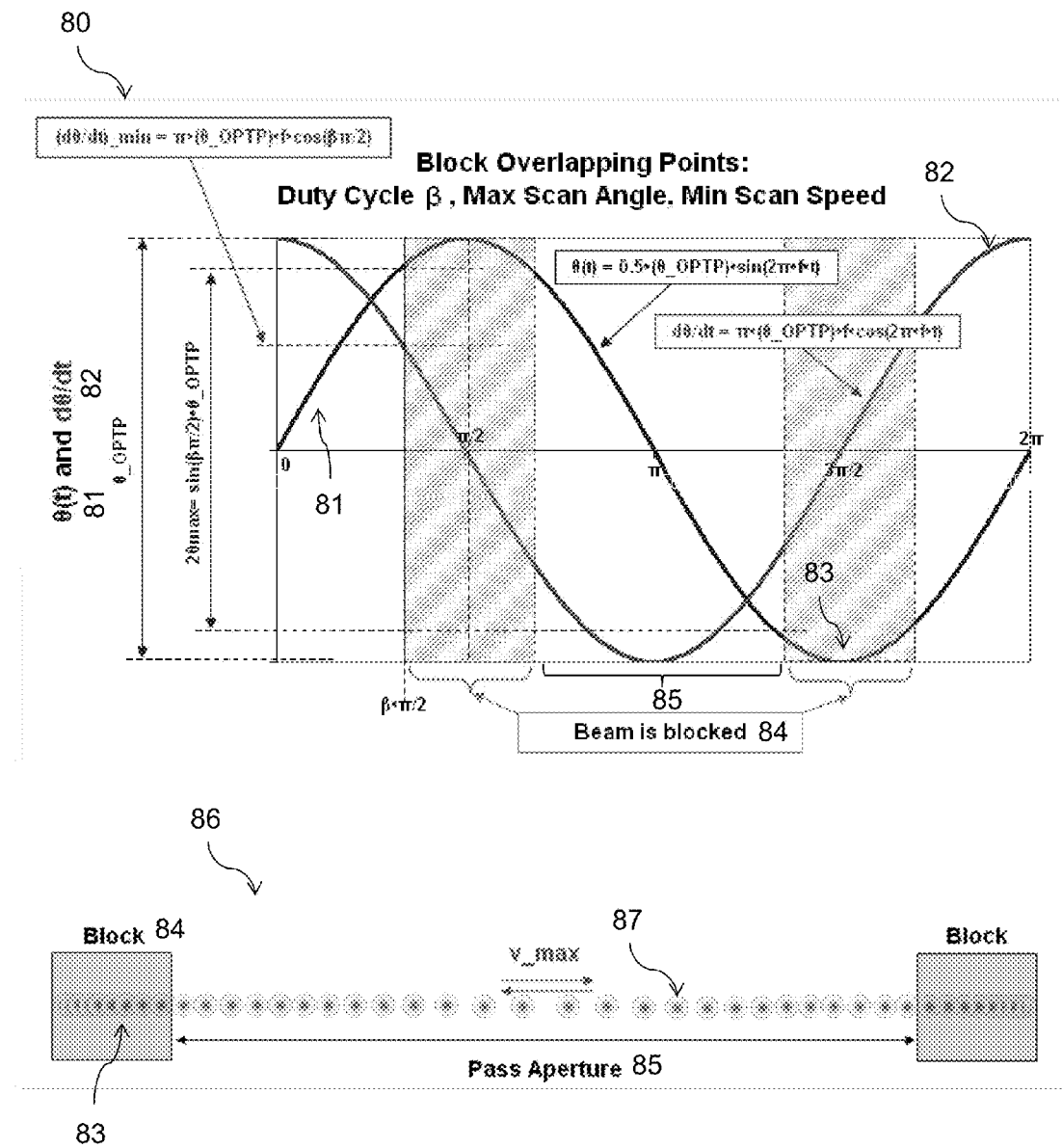
FIG. 6 is a graph related to resonant scanning operation according to certain embodiments.

As illustrated in the graph 80 of FIG. 6, the scanning provided by a resonant optical scanner 3 is characterized by a sinusoidal curve. Thea resonant optical scanner may oscillate at a frequency between 200 Hz and 21000 Hz. The curve 81 represents the scanning angle of a resonant scanner 3 and curve 82 represents the scanning speed. As shown by the curve 82, the scanning speed continually varies such that the density of laser spots along the scan line will vary. Accordingly, that the distribution of laser pulses is uneven.

For instance, scan line 86 illustrates the sinusoidal distribution of laser spots 87 provided by a resonant scanner 3. Whether a scanning speed reaches zero or a maximum speed, laser pulses will continue to be emitted at the same rate. Undesirable spot overlapping 83 occurs when the scan speed is at and near zero. This may lead to areas of tissue that are overcut from an excess number of laser pulses.

Some embodiments overcome this by preventing overlapping spots 83. In one embodiment, the overlapping spots 83 are emitted but physically blocked 84 from scanning a target material to provide a higher quality tissue cut. During time period 85 between the blocked periods 84, the laser is not blocked and passes an aperture of the laser system.

Figure 7:
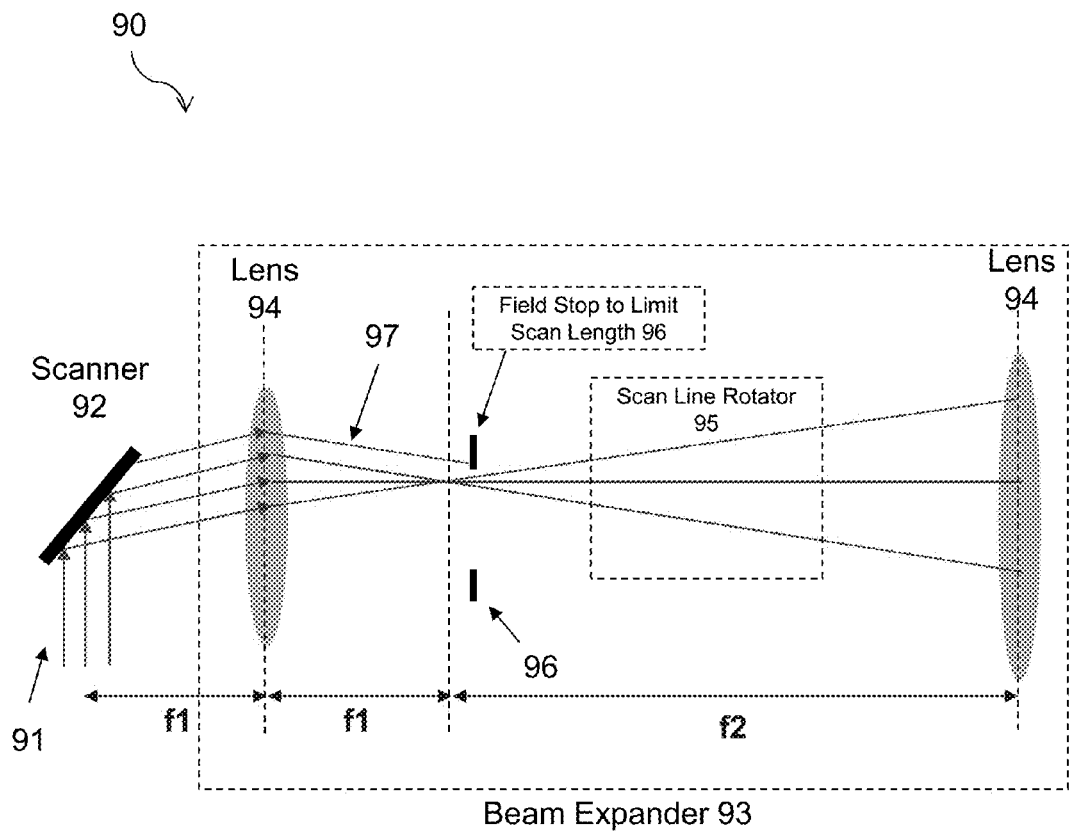
FIG. 7 illustrates a schematic view of a beam delivery system according to certain embodiments.

FIG. 7 illustrates a schematic view of a beam delivery optics system 90. A pulsed laser beam 91 emitted by a laser source (not shown) reaches a resonant optical scanner 92 and is delivered into a beam expander 93. The beam expander includes a lens 94 that focuses the beam through a scan line rotator 95 and another lens 94. A predetermined portion 97 of the beam 91 is blocked by a field stop 96 to limit the scan length of the raster.

The pulses 97 may, for example, correspond to the blocked portion 84 overlapping spots 83 in FIG. 6. In this manner, undesirable light pulses are physically blocked within a beam expander 93 as the light focuses, ensuring that laser spots are not concentrated too densely within a spot or scan line area. The blocker or field stop 96 may be provided near but not precisely at the focal plane so as to prevent the blocker from burning. It is noted that conventional scanners do not exhibit sinusoidal wave characteristics such that those systems have no need to provide blocking.

Figure 8:
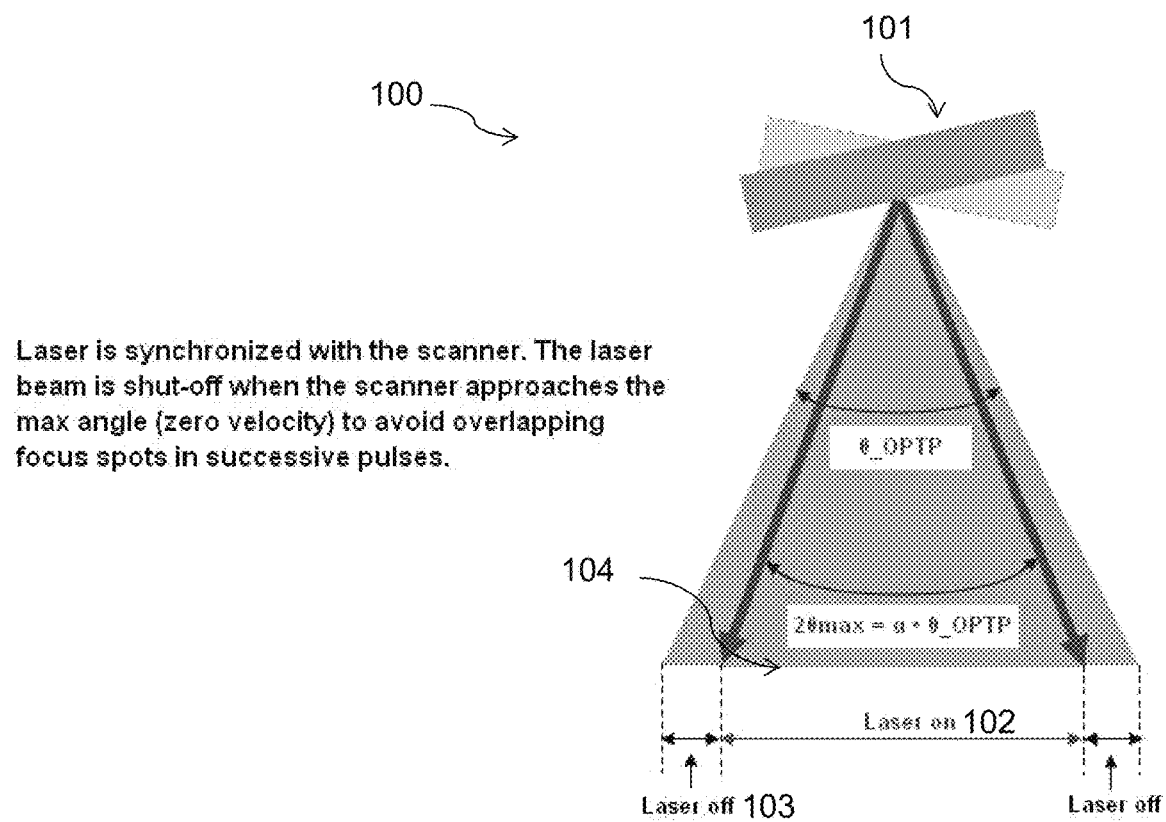
FIG. 8 illustrates a schematic view of a scanner according to certain embodiments.

In an alternative embodiment, FIG. 8 illustrates a schematic view of a scanning system 100. A resonant optical scanner 101 is illustrated as vibrating so as to produce a scan line 104. A laser (not shown) producing laser pulses is synchronized with the frequency of the scanner 101 such that the laser is turned on 102 and off 103 when the scanner 101 approaches a predetermined maximum scan angle with a corresponding zero velocity in order to prevent overlapping focus spots in successive pulses.

Equation 1 is an algorithm for determining a duty cycle that is a percentage time that a beam passes an aperture, scanner frequency, optical peak-to-peak angle, a pupil diameter for given laser pulse repetition rate, and desired numerical aperture of the optical system. An example for NA=0.6 is provided below:

$$2400\cos(\frac{\pi}{2}\beta)[\theta_{OPTP} \cdot f_{SCAN} \cdot D_{PUPIL}] \geq f_{LASER} \qquad \text{(Eq. 1)}$$

Equation 1 guides the selection of resonant scanner parameters for a spot edge to edge condition, as shown in Table 110 in FIG. 9. Table 110 highlights the values that satisfy a requirement of spot size (FWHM=1.1 um) and avoiding laser spot overlap.

In some embodiments, a fast raster scanning pattern can be generated by synchronizing a plurality of resonant scanners in the laser system 1. For example, FIG. 10 illustrates a pair of perpendicular scanning resonant mirrors 120 with the same frequency, the same amplitude, and a phase difference of 90° between them that generate a fast circular scan line 121, for example.

A circular scan line exhibits a number of advantages including equal spot distribution so as to render blocking techniques redundant. In this case, the linear speed of the scanning is a constant, and is equal to the maximum speed that can be achieved with a single scanner. Therefore, there is no need to block the "zero speed" points as in the case of using a single scanner, and the duty cycle is 100%, i.e., 100% of laser pulses will be used for tissue dissection. Furthermore, a circular scan line ensures that targeted tissue receives two pulses with each pass, thereby ensuring a cut. Also, a circular scan line is also well matched against another curve, such as the edge of a circular surgical field.

The first scanner may be provided for the x axis while the second scanner may be provided for the y axis in different phase relation to generate a plurality of two-dimensional scan patterns that may obviate the need for a scan line rotator. The use of at least two scanners may generate a line oriented at any desired angle, circle, curve, etc.

Another arrangement of synchronization is to synchronize two parallel scanners so that the optical peak-to-peak angle is doubled in comparison with a system using one resonant scanner. In yet another embodiment, a plurality of resonant scanners may be synchronized to extend the scanning range of a single scanner.

Next, embodiments of a scan line rotator will be discussed. A resonant scanner produces a one dimensional scan line in a single direction. However, this output is not ideal for cutting near an edge or curve of a surgical field. For example, when an optical field is provided along an edge of surgical field, the line must be rotated to fit the curve.

Therefore, a scan line rotator is configured to rotate the scanned line in a desired orientation.

Figure 11:
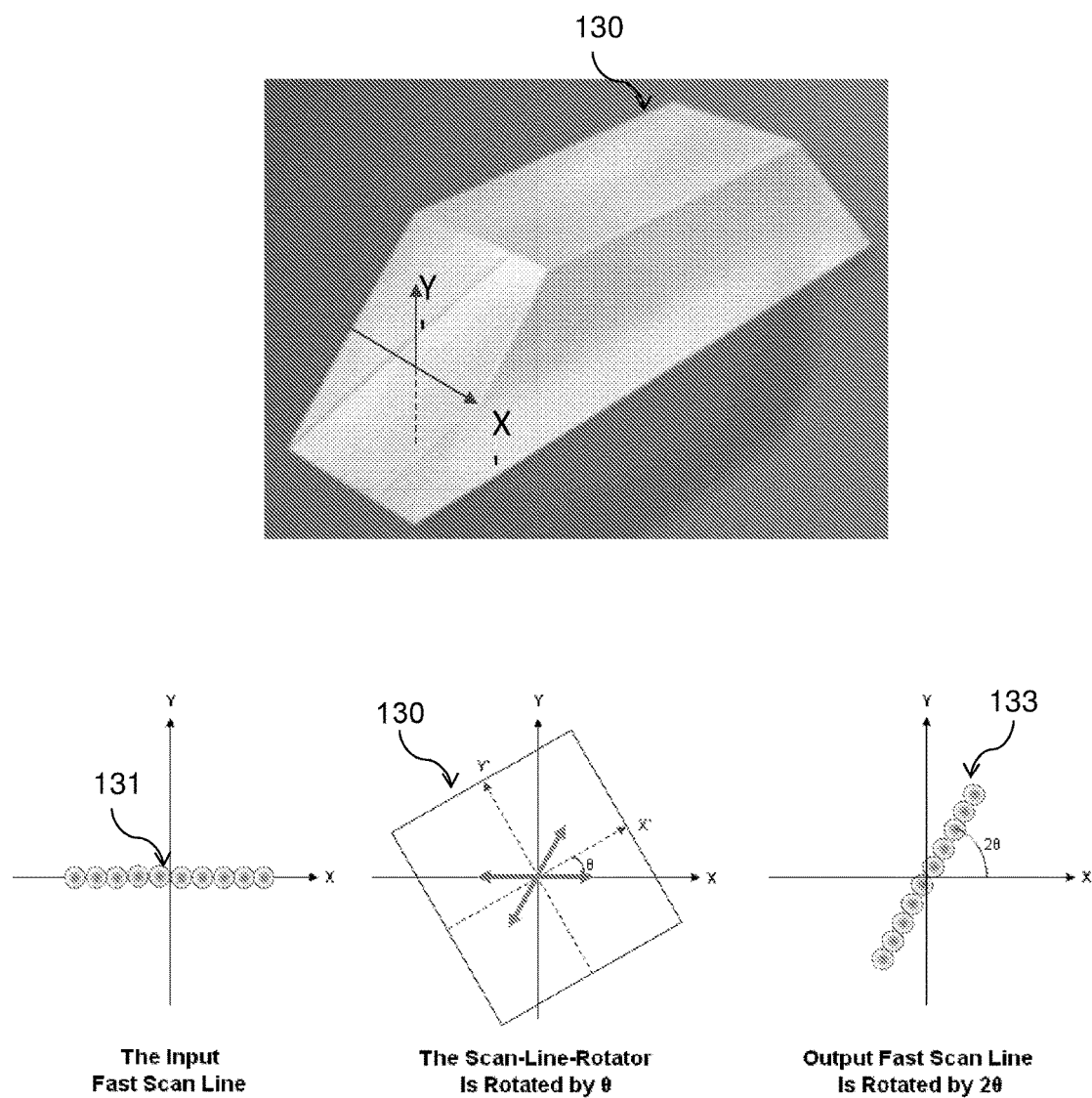
FIG. 11 illustrates a perspective and graphical view of a scan line rotator according to certain embodiments.

FIG. 11 illustrates a perspective view of an exemplary scan line rotator 130 and graphical views of a scan line rotated by a scan line rotator. The scan line rotator 130 is a Dove prism, but may also be a Pechan prism or a set of mirrors. Implementations of a scan line rotator using a Dove prism or Pechan prism are cost-effective, compact and lightweight, and contribute to a compact laser system. The input scan line 131 is a non-rotated scan line. As the scan line rotator 130 rotates by an angle θ, the input scan line 131 will follow the rotation and the output scan line will be rotated by 2θ.

The output raster 133 is thus oriented in any desired direction to scan an entire optical field. In combination with an XY stage, the system 1 may scan an entire treatment area. Tissue fibers may sometimes be aligned in certain directions that favor a rotated raster. Furthermore, a scan line rotator allows for flap creation, cornea incisions, IEK, inlays, rings, etc. and procedures such as SmILE or ReLEx procedure.

Figure 12A:
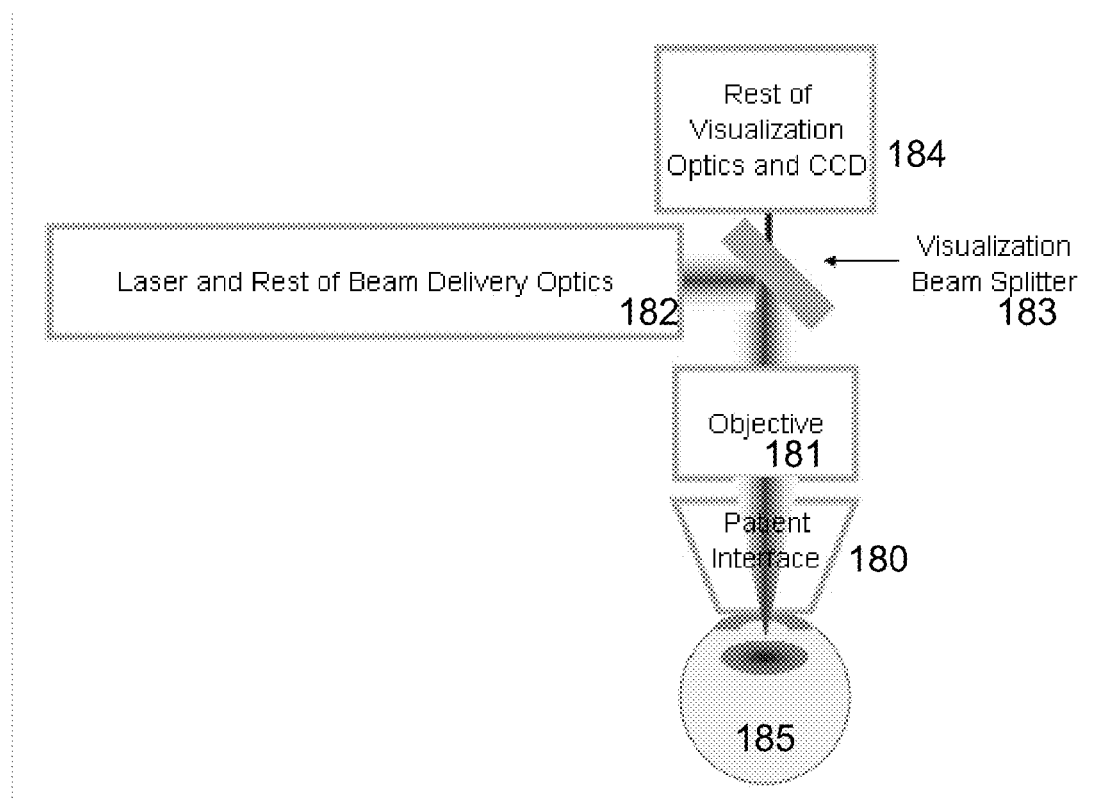
FIGS. 12A-12C illustrate various patient interfaces used with certain embodiments.
Figure 12B:
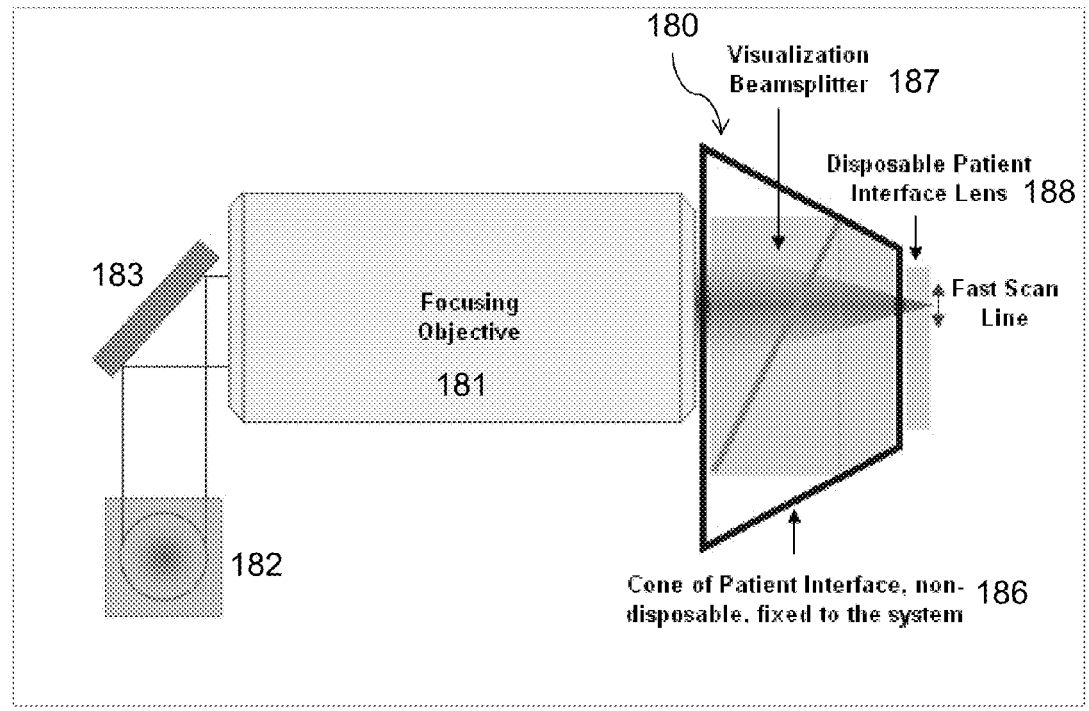
Figure 12C:
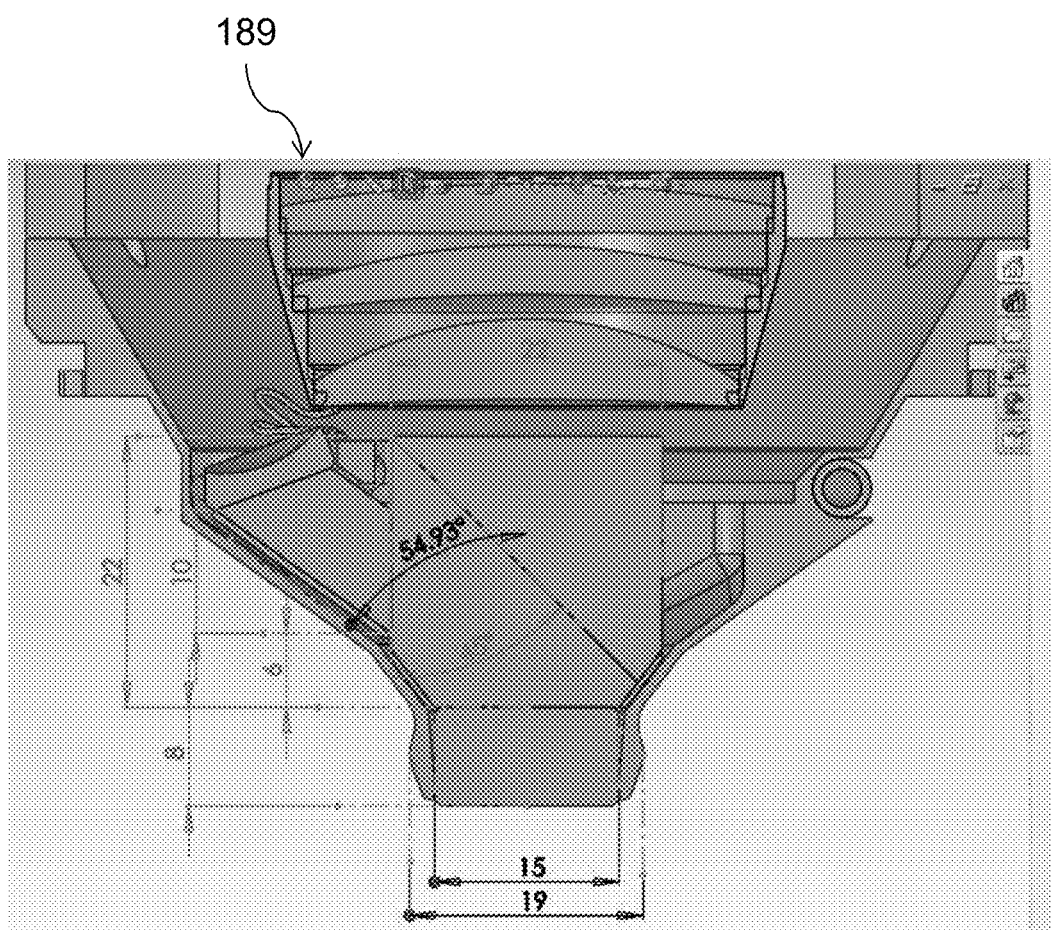

FIGS. 12A-12C illustrate interfaces which may be employed with the present embodiments. For many prior art femtosecond laser workstations, the field of view for visualization optics 184 such as a CCD and video microscope is similar to the field of view of surgical beam scanning such that a visualization beam splitter 183 is positioned above the focusing objective 181, patient interface 180, and cornea 185. In this configuration, the size of the optics system, including both beam delivery 182 and visualization 184, is generally large and unwieldy.

FIG. 12B is a schematic cross-sectional view of the patient interface 180 that includes a cone 186 that is fixed to the system, a visualization beam splitter 187, and a disposable patient interface lens 188. A beam splitter 187 is coated for reflecting the visual spectrum but passes light for the femtosecond laser wavelength and is placed inside the cone frame 186 of the patient interface 180 fixed to the system. The ocular video microscope optical path goes through this beam splitter. Accordingly, a cutting process may be viewed and/or displayed in-situ.

FIG. 12C is a cross-sectional view of another patient interface 189 where a visualization beam splitter is placed inside the cone of the patient interface 189. This design is sufficient for a limited range of numerical aperture of surgical beam, for example, NA≤0.4. For yet greater NA, such as NA=0.6, some oblique rays of the surgical beam will experience high loss at the beam splitting surface (the 45° surface as shown in the diagram). As the NA increases, the size of the beam splitter will need to increase as well.

The visualization optical path may be provided outside the cone of the patient interface in a side channel. However, for deep set eyes, the side channel has to be placed much higher, increasing the size and bulk of the beam splitter. Consequently, the outer dimension of the patient interface cone will not fit the normal anatomy of a patient eye and is thus inadequate based on human factors. Simply put, a user's facial features will occupy the same space as the enlarged patient interface necessary to accommodate a visualization beam splitter for high NA laser systems.

Figure 13:
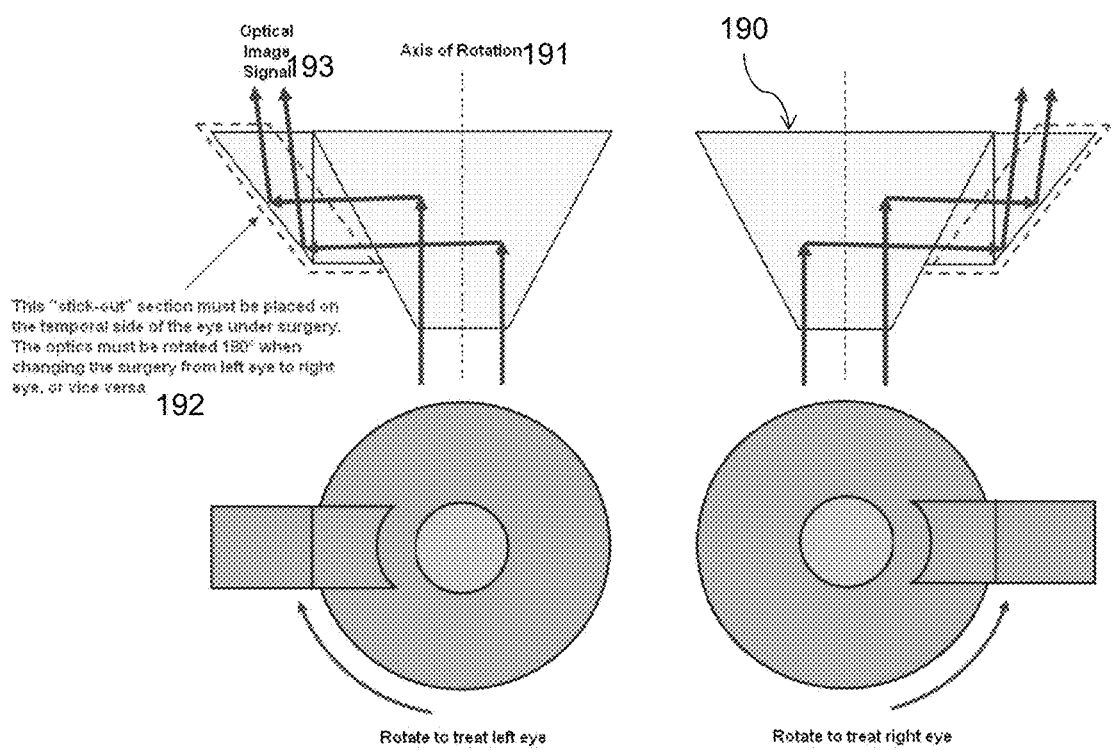
FIG. 13 illustrates a patient interface according to certain embodiments.

FIG. 13 illustrates a patient interface according to certain embodiments. To overcome the issues described above, a rotatable protruding portion 192 of the patient interface 190 is rotatable about an axis 191 and provided on the temporal side of the patient head to allow the optical image signal 193 to exit the patient interface. To fit both left and right eyes of a patient, the visualization optics (including the beam splitting optics, the patient interface 190, the imaging optics, and the CCD) are rotated 180 degrees in accordance with treating left and right eyes, respectively. In this manner, the larger visualization beam splitter elements are better positioned to avoid conflict with a user's face.

Figure 14A:
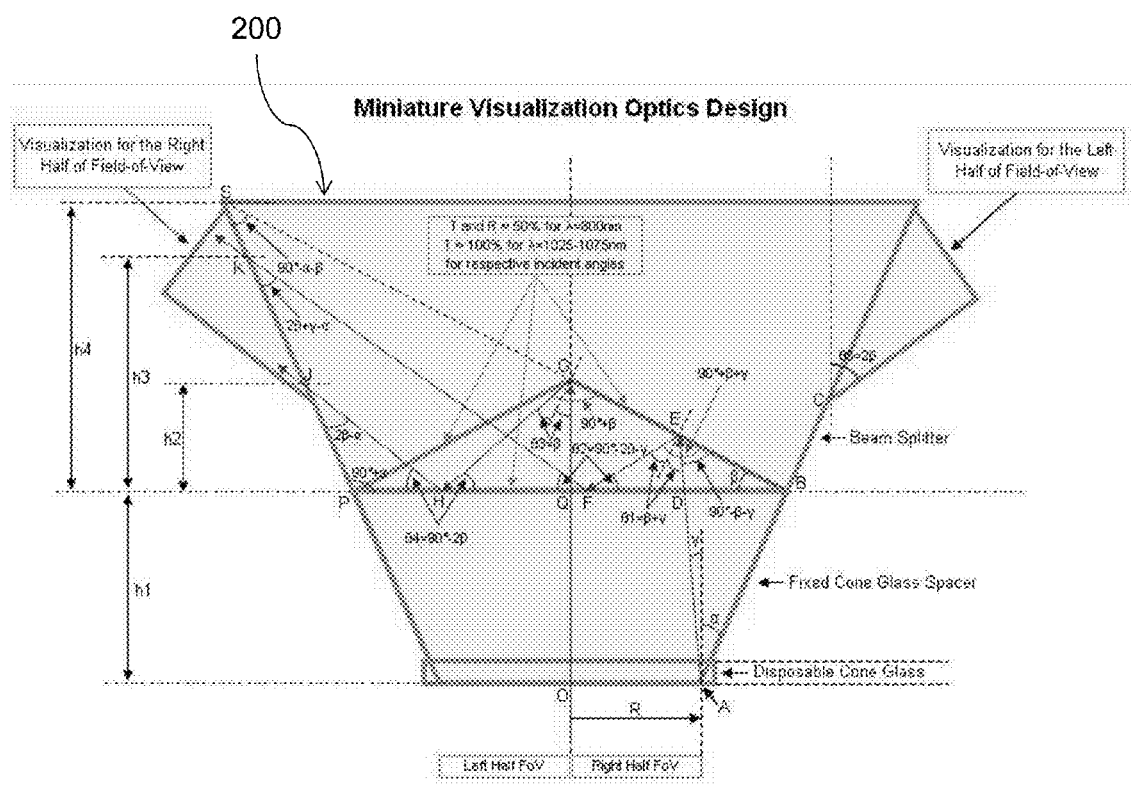
FIGS. 14A-14B illustrate beam splitter optics according to certain embodiments.
Figure 14B:
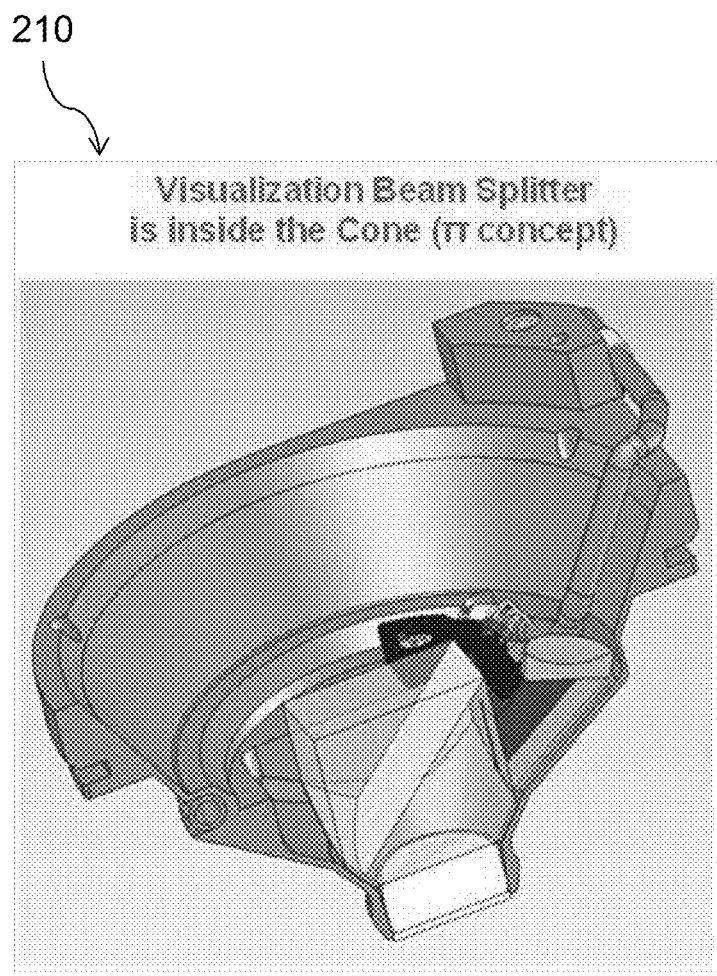

FIGS. 14A-14B illustrate beam splitting optics according to certain embodiments. A patient interface 200 is provided including two beam-splitting surfaces, BG and GP. These two surfaces divide the full field of view into left half and right half, and form two separate visualization channels. As a result, this reduction in the size of the channels allows the channels to fit into the cone of the patient interface 200 such that no rotation of the visualization beam splitter is needed when treating left and right eyes. Furthermore, the channels support high NA (NA=0.6) surgical beams. FIG. 14B illustrates a cross-sectional perspective view of the patient interface 210 with a visualization beam splitter in the cone.

An interface for coupling a patient's eye to an ophthalmic surgical laser system includes a lens cone defining a first plane surface coupled with a delivery tip of the ophthalmic laser system. The lens cone includes an apex ring coupled to the first plane surface. The apex ring includes a distal end including a first receptacle configured to receive an attachment ring, the attachment ring configured to overlay an anterior surface of the patient's eye. The first receptacle and the attachment ring may be disposable. A central cavity is provided to receive the lens cone. A contact lens may applanate the anterior surface of the patient's eye.

One or more beam-splitter optics are provided to allow a pulsed laser beam to pass through the interface to a focal point of the target in the patient's eye. The beam-splitter optics may include one or more multi-facet beam-splitter optics and a side-imaging optical channel that is configured to rotate to a temporal side of the patient's eye. Alternatively, the beam-splitter optics may include dual imaging channels. The beam-splitter optics may be provided to manipulate non-telecentric imaging rays at a full optical cone angle equal to or greater than fifteen degrees.

FIG. 15 illustrates a table of visualization parameters according to an embodiment of the present embodiments. The specific numerical values for the half cone angle (α), the beam splitting surface angle (β), and the edge ray incident angle (γ), and the geometry dimensions of the visualization beam splitter are given in table 220.

Figure 16:
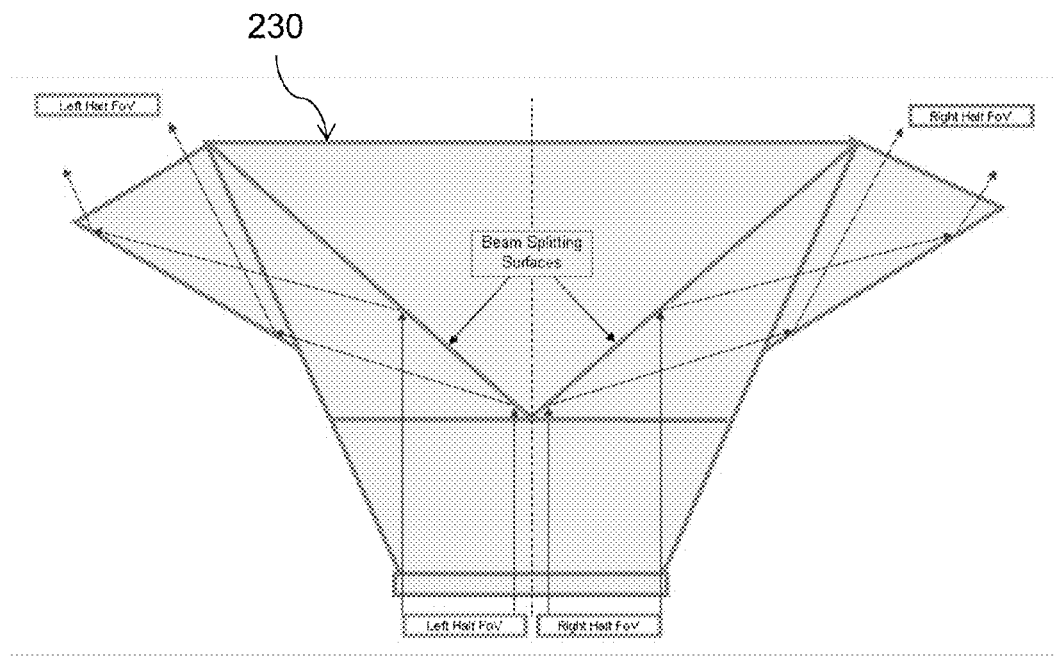
FIG. 16 illustrates beam splitter optics according to certain embodiments.

FIG. 16 illustrates beam splitting optics according to certain embodiments. The patient interface 230 in FIG. 16 divides the full field of view into two halves, images the two halves into two different optical channels, and processes to combine the two half-images together to reconstruct the full field of view. In this manner, the entire visualization beam splitting optics can be placed inside the cone of a compact patient interface 230.

This approach of dividing the full field of view into several smaller fields, and then combining the images of the smaller results to reconstruct the original large field of view may also be applied to measurement such as an optical channel for Optical Coherence Tomography, for ophthalmology surgical lasers including but not limited to femtosecond laser workstations.

Tissue Thickness Measurement Examples

The systems and methods here may be used to measure corneal thickness or other anatomy to prepare a treatment plan for any numerous treatments such as LASIK, PRK, intra stromal lenticular lens incisions, cornea replacement, or any other treatment. By reducing the power of a femtosecond laser from an incision power to a non-incision powers such as less than 40 milliwatts for example, a backscatter of the laser may be measured to calculate distances. These distances may be between an interior boundary and an exterior boundary of a cornea. Such systems and methods can produce thickness calculations that are accurate to a 1 μm resolution for example.

The thickness measurements may be used for various purposes. Some embodiments may be used to measure other parameters in the eye or other anatomy. Some embodiments may be used to identify patients or identify the appropriate eye to treat by comparing calculated eye tissue thickness with previously calculated thicknesses for a specific patient or eye. Some embodiments may be used to ensure a patient's cornea is thick enough to allow incisions and heal correctly. Some embodiments may be used to measure corneal thickness both before and after treatment. Some embodiments may be used to replace a cornea on a patient needing a transplant.

Figure 17:
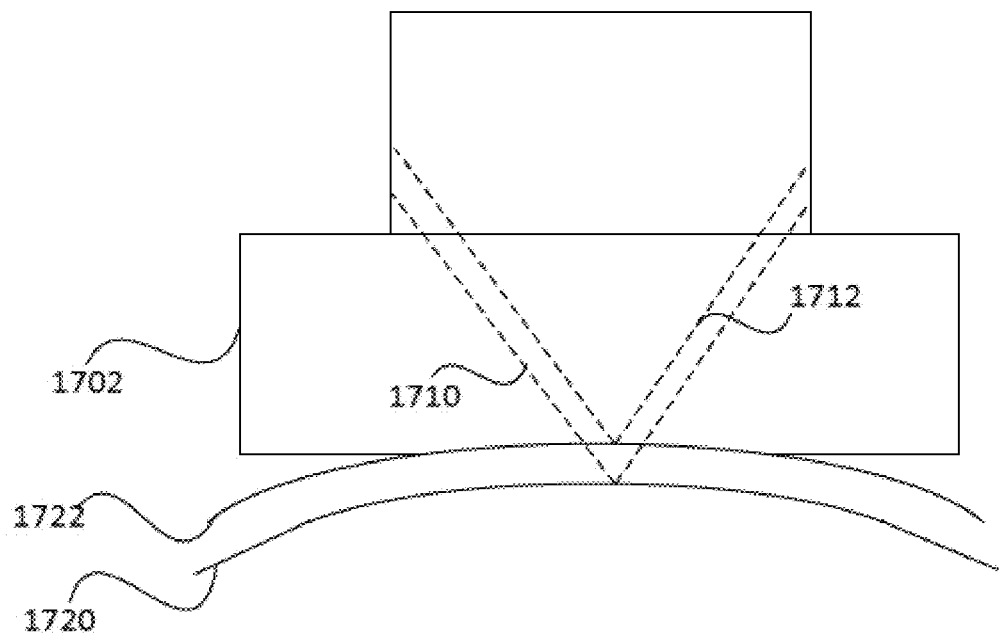
FIG. 17 illustrates an example corneal back scatter pattern according to certain embodiments.

FIG. 17 shows a simplified diagram of how the laser systems here could be used to focus a laser beam at various depths in the eye and capture reflected backscatter from the interior 1710 and exterior surfaces or sides 1712 of a cornea. In the example, the cornea has an interior boundary or side 1720. The cornea also has an exterior boundary or side 1722. By calculating a time it takes for the laser to sweep through the cornea the system may calculate the distance between the corneal boundaries. The system can receive and detect changes in the reflected backscatter as the focal point moves from the interior of the eye toward the surface of the cornea and through the cornea. As the laser focal point moves in and through different tissues the beam may scatter and reflect differently. Such energy can be captured by a beam splitter and analyzed by a detector. The detector may gather information of reflected power changes over time as the z axis focus moves from inside the anterior chamber of the eye, through the lens, and through the corneal stroma. A power to time chart may be calculated showing changes or peaks in power when the focus of the laser pulse passes different tissues.

For purposes of simplicity only, no epithelial layer, endothelial layer or other structures are shown in the eye in example in FIG. 17 but any of these structures could be measured in the same or similar ways.

As shown in FIG. 17, the femtosecond laser patient interface 1702 could be used in measuring the corneal thickness in both an applanated or docked position on the eye as shown in FIG. 17, or free (not shown), as in some distance from the eye. It could be used in a liquid interface as well (not shown). In some embodiments, the system could adjust or correct of the various distances or media the beam travels would need to be entered in the calculations.

Figure 18:
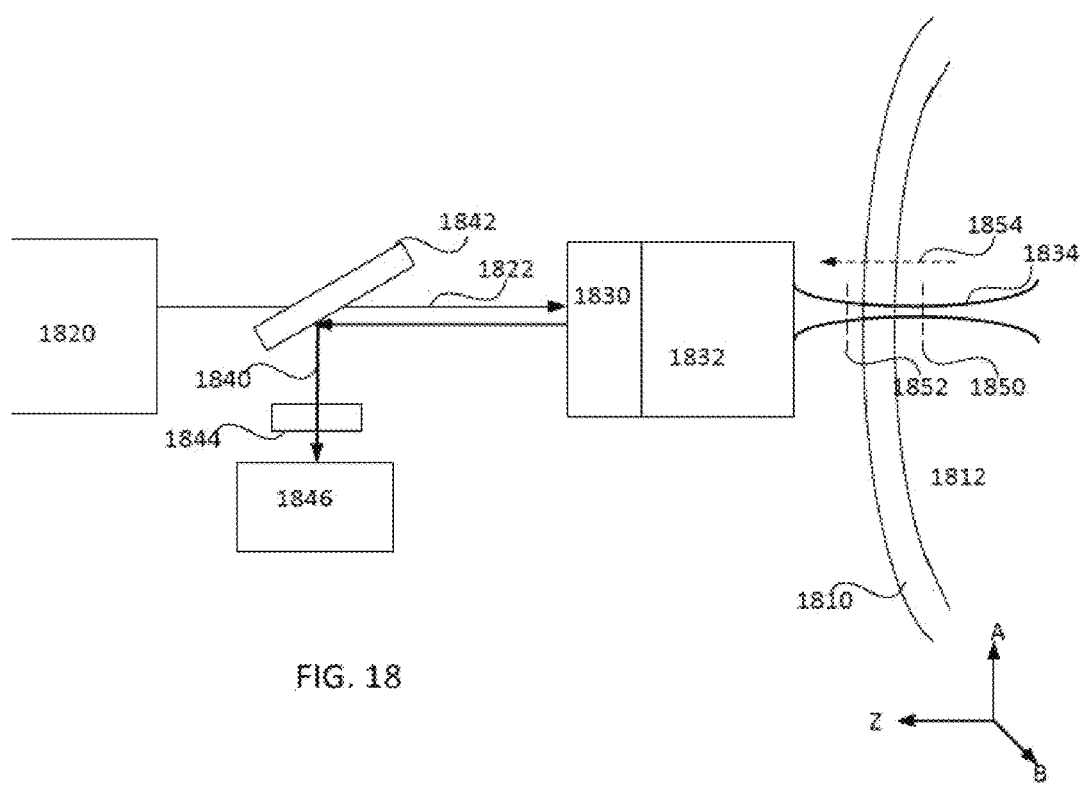
FIG. 18 illustrates an example system measuring a corneal thickness according to certain embodiments.

FIG. 18 shows an example system for measuring a cornea 1810 thickness or other tissues. The example shows how the system is able to focus a laser beam in the z axis and move the focal point of the laser beam in the z axis to sweep or move through various tissues 1854. For example, by sweeping 1854 the focus of the laser focal point in the z axis direction from the interior chamber 1812 of the eye, through the cornea 1810, the system is able to detect received power of the reflected backscatter.

In the example, the Femtosecond laser 1820 generates a low power pulsed laser beam 1822. It should also be noted that the beam need not be pulsed but in pulsed embodiments, individual pulses may be generated so they may be identified and measured and/or counted by the system. In such examples, the detector could be used to identify individually generated pulses and thereby reduce the noise of the back scattered energy, to more precisely determine the corneal thickness. In some embodiments, the laser beam may have an NA depth of focus between 0.3 and 1.3 NA. Some embodiments may use a laser wavelength between 300 μm and 1200 μm. A preferred embodiment may be 345 μm or 1030 μm. Some embodiments may use a laser power at the focal point below 40 milli watts or in other words below the photo disruption threshold for the eye, as no incision is intended, merely a backscatter of the energy. In some embodiments, the laser power at the focal point is between 20 and 40 milliwatts.

In FIG. 18, the beam 1822 passes into the Z Control 1830 and then the focusing optics 1832 of the laser system. The laser beam 1834 enters the eye and is focused in the anterior chamber 1812. From there, the laser beam focal point is moved or swept along the z axis direction 1854 from inside 1850 outward 1852 at a known speed. The reflected back scatter 1840 may then be reflected by a beam splitter 1842 and directed through a confocal aperture 1844 into a detector 1846. The detector 1846 may receive the returned backscatter energy and measure the power of the energy as described in FIG. 19.

It should be noted that in certain example embodiments, the laser and the beam splitter 1842 could also be polarized. Such polarization may be used to restrict the reflected back scatter and reduce the noise of the detected power spikes. A circular such as clockwise, counterclockwise, or a linear or other polarization could be used to reduce the noise of the received beam and more precisely determine the corneal thickness.

The systems and methods could also be used to measure the depth of other tissue such as the epithelial layer as well as the cornea or any other tissue that would create a reflected backscatter.

Figure 19:
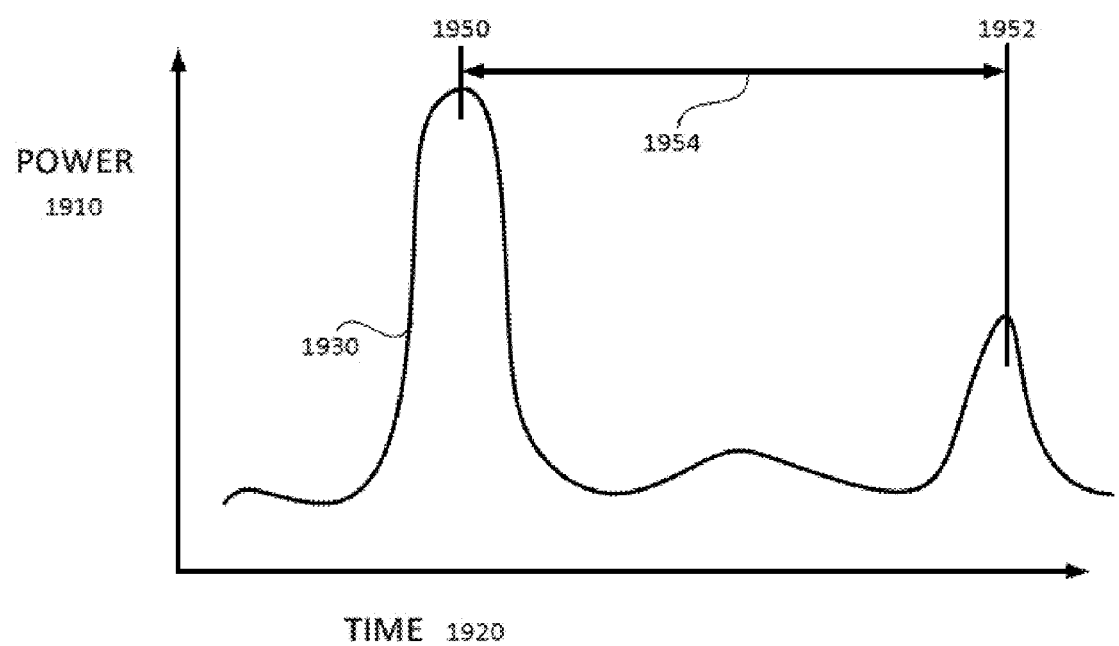
FIG. 19 illustrates an example corneal backscatter power plot according to certain embodiments.

FIG. 19 shows an example corresponding energy return graph as measured in the example detector 1846 from FIG. 18. The energy analyzed by the detector may be plotted on a graph showing power or energy returns as the laser focal point is moved or swept from the inside of the eye 1850 outward 1852 through the cornea or other tissue. The graph on FIG. 19 shows Power 1910 of the received backscatter as a function of Time 1920 as received in the example by the detector. The energy return 1930 is plotted in this visual for example purposes only. A visual graph is not necessary for the system to detect energy anomalies or peaks and calculate the depth of any tissue such as the cornea. In this example, the resulting received backscatter power from the detector shows a spike in received power 1950 as the focal point is moved or swept from the interior of the eye and passed through the interior side or boundary of the cornea. Another appears when the laser beam focal point passed from the corneal stroma 1952 into the epithelial layer or beyond.

Using these two peaks and a known speed of the laser focus point sweep in the Z direction, any kind of computing device can calculate time between the power spikes 1950 1952, and thereby the distance 1954 between the interior and exterior boundaries or sides of the cornea.

Map of Corneal Thickness

From multiple measurements of the thickness of a cornea in the lateral A and B directions, a map may be produced representing the corneal thickness which may be used in preparing a treatment plan for any numerous treatments such as LASIK, PRK, intra stromal lenticular lens incisions, cornea replacement, or any other treatment.

Figure 20:
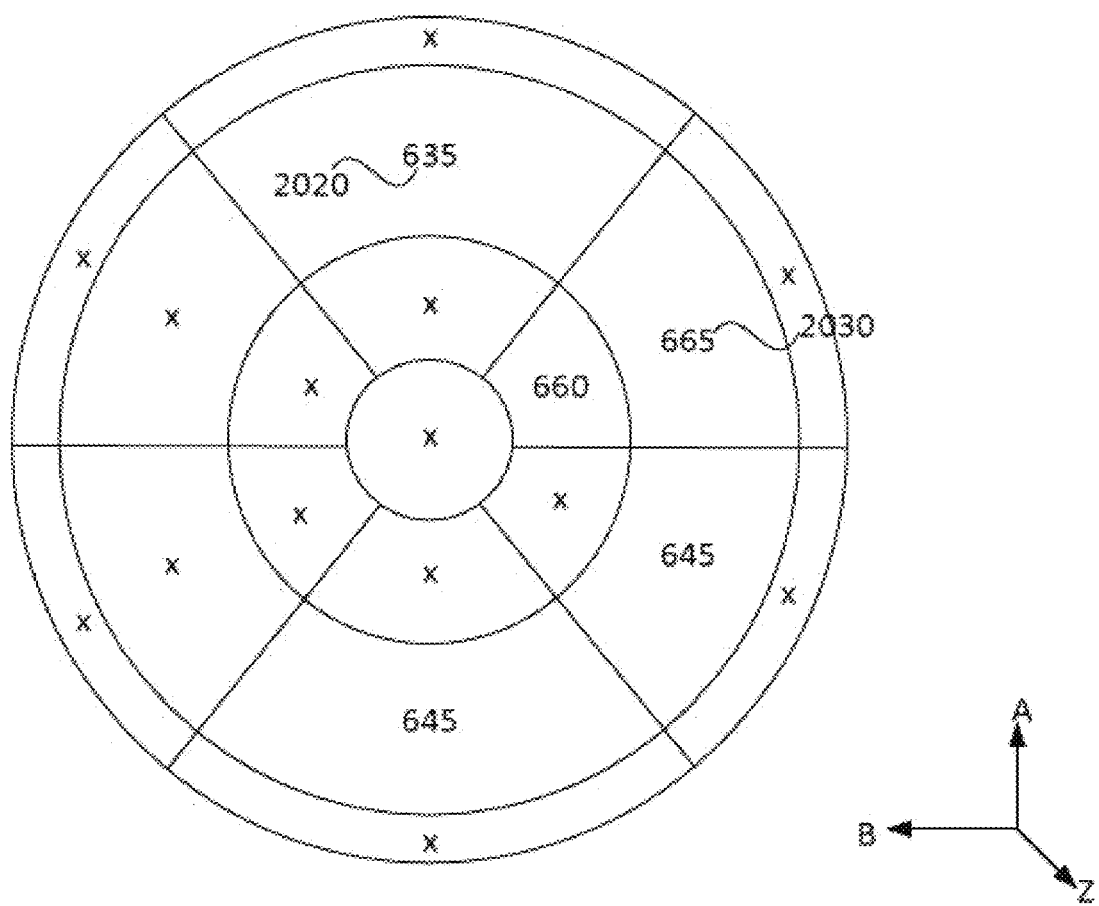
FIG. 20 illustrates an example corneal thickness map according to certain embodiments.

FIG. 20 shows an example map of different corneal thicknesses as measured in various parts of the eye. In the example, one type of map is shown, but any kind of map or chart of the measured eye thicknesses could be created broken into any of various regions or zones. The thicknesses in the various quadrants or areas may be measured and plotted on a map and indicating different calculated thicknesses of the cornea. For example, FIG. 20 shows a thickness of 635 µm at quadrant 2020 and a thickness of 665 µm in quadrant 2030. Other areas of the map may or may not indicate the thicknesses as the laser progresses in measuring various areas.

In some embodiments, a heat map may also be created using any of the variously plotted thicknesses showing color or shaded areas corresponding to particular thicknesses. In some embodiments, interpolations of measurements may be used to estimate thicknesses of portions of the cornea which are not directly measured. And kind of visualization of the calculated thicknesses may be used.

The measurements may be used to design a treatment plan for a patient, for example, if a cornea is too thin, certain treatments may not be feasible. The measurements may be used to positively identify a patient, to ensure treatment is planned correctly for a particular eye, and/or patient.

For a map of cornea thickness any number of mapped segments may be measured and calculated by the system depending on the treatment and desired resolution.

Alignment

When a patent prepares for treatment, various measurements and preparation of the eye may occur. During this preparation, using the systems and methods here, a corneal thickness map may be calculated. As such preparation may occur when the patient is not in the same position as when the treatment is undertaken, a later alignment of the treatment device may be necessary. For example, the patient may be sitting when preparing for treatment but lying down when under treatment. For example, the patient may not have anything touching the eye when preparing for treatment but have a patient interface pushing or ablating the eye during treatment. This may result in deflection of the cornea while ablated and offset the pupil.

These variations in condition may alter the appearance of the eye or distort its orientation in the head. Such variations and changes may misalign the treatment devices as compared to the preparation unless a correction of the alignment is undertaken.

It is to be assumed that an ablated eye cornea thickness is the same as the natural unablated eye, and that the interior of the eye absorbs and deflects the pressure placed on the eye from the docked treatment device. However, the cornea may stretch, move or otherwise deflect when ablated. It is these movements that are calculated in the comparison and compensated for.

Such correction of the alignment may be made using two or more maps of a corneal thickness for an individual eye, where one map may be made while a patient is sitting upright in a natural an unablated state preparing for treatment and the second while laying down when the treatment device is docked to the eye in an ablated state. The system may compare the two maps to correct the alignment of the treatment laser while in the treatment condition.

Corneal Transplant Examples

Certain embodiments may be used in corneal transplants by measuring from the interior toward the surface of the cornea instead of measuring from the surface down. This is because when removing cornea for a transplant, it is preferable for the operator to know how much cornea is left on the eye and remove the remainder, than to remove a certain amount of cornea, hoping to arrive at a left over layer that was not directly measured.

Corneal transplants require a section of the cornea to be removed from the patient so that section can be replaced. Results may be enhanced for such procedures when the amount of cornea removed leaves only a thin layer on the eye. For example, it may be beneficial to remove all but 50 µm of corneal tissue and replace that removed section with a replacement transplant cornea.

In order to determine how deep to make the cut to remove the cornea section, other systems would use a measurement from an exterior of the cornea and measure down into the cornea to an estimated depth. Then a laser would remove that section of the cornea. This other method allows the operator to know the depth of the removed section, but it does not allow the operator to know the depth of the remaining tissue. This other technique may result in the remaining tissue being either too thick or too thin for desired results. Further, such techniques may get too close or even damage the cornea endothelium layer on the interior side of the cornea.

Alternatively, using the systems and methods described here may allow a precise measurement from the interior of the cornea toward the surface, instead of measuring down from the exterior of the cornea, and guessing the depth to cut. Such methods and systems may allow the laser to make an incision at a known measured distance from the endothelium layer in the cornea, thus allowing removal of all but a known amount of tissue.

Figure 21:
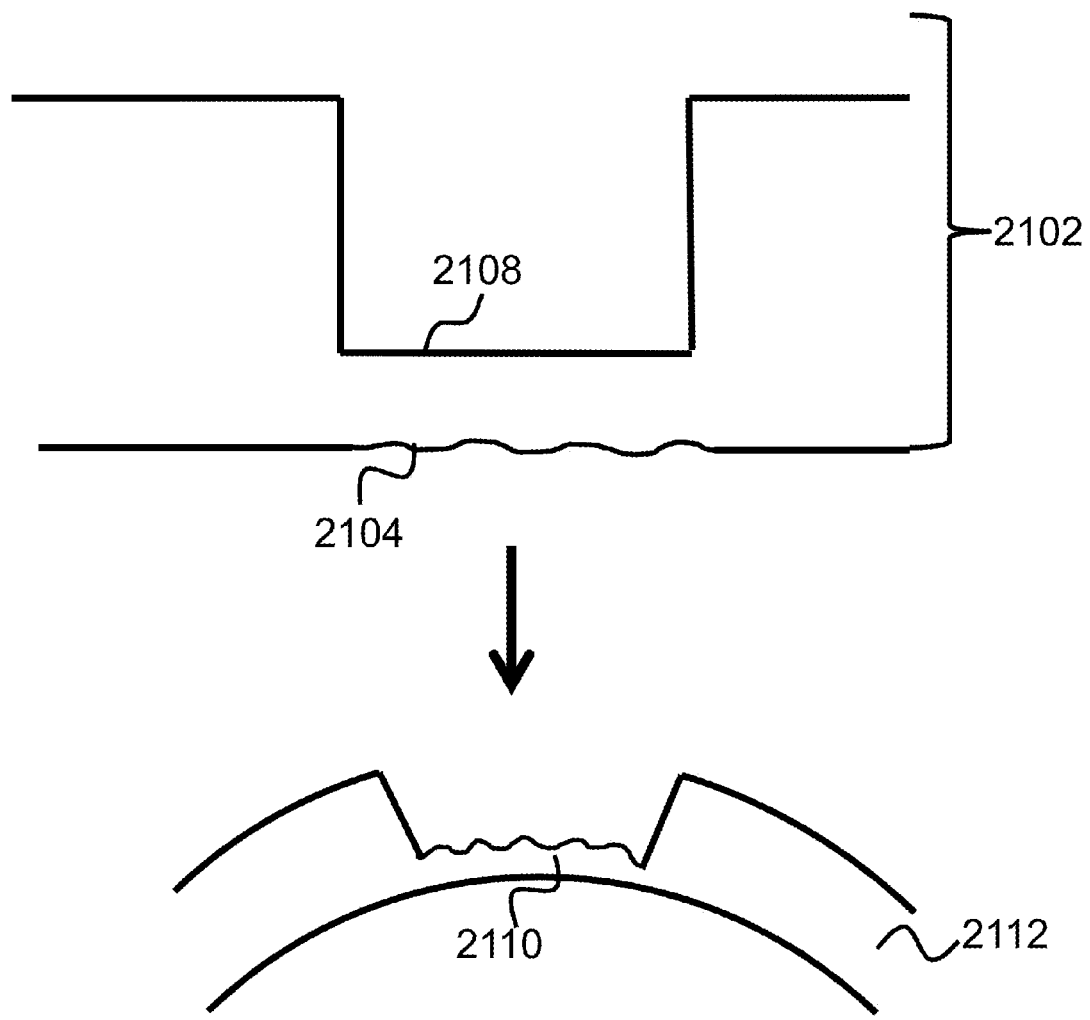
FIG. 21 illustrates an example corneal thickness wrinkle correctable by certain embodiments.

Another embodiment of the systems and methods here may be compensation for corneal folds which may occur when the system is docked to a patient for treatment. FIG. 21 shows an example of such corneal folds 2104 that may occur when the patient interface (not shown) docks with the cornea 2102 of a patient and presses it into a flatter shape as shown in the side view cut-away of FIG. 21. In so docking, the cornea becomes applanated and possibly distorted by the pressure while pushed into a flatter shape than the cornea in its free state. When the cornea is so flattened, corneal waves, folds, or wrinkles 2104 may result on the anterior side of the cornea. Incising a flat cut 2108 on the cornea in this state might then result in a distorted cut 2110 when the cornea is returned to its natural, free and undocked state 2112. This is an undesired effect, and one that can be compensated for using the systems and methods described here.

Figure 22:
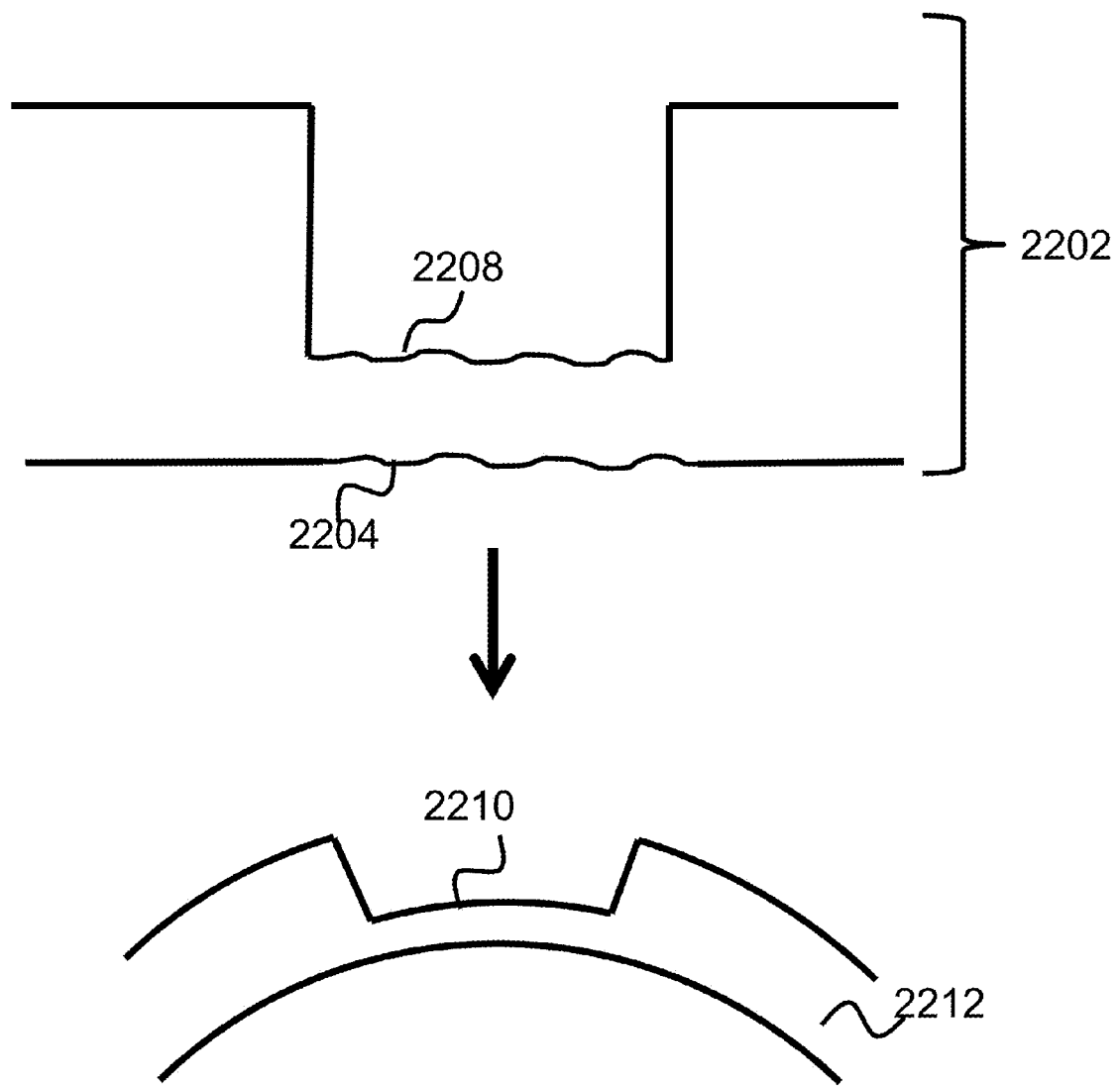
FIG. 22 illustrates an example corneal thickness wrinkle correctable by certain embodiments.

FIG. 22 shows an example, similar to FIG. 21 but in this case, where the systems and methods here are used to correct for corneal wrinkles 2204. As shown in FIG. 21, in FIG. 22, when the cornea 2202 as shown in a side view cut-away, is applanated or docked by the system, it may result in corneal folds in the anterior side 2204. But using the systems and methods here, a precise measurement may be made of the anterior corneal folds 2204 and the system could be used to incise a cut 2208 that follows these wrinkles 2204 instead of being flat. The result may be a more uniform or smoother surface 2210 when the cornea 2212 is undocked and returned to its natural state. Such a smoother surface may produce better results for the patient than by incising a cut as in FIG. 21 which does not follow the wrinkles in the anterior applanated cornea.

It should be noted that the wrinkles shown in FIGS. 21 and 22 are simplistic two dimensional representations of what a corneal fold may look like. The systems and methods here may be used to measure three dimensional corneal folds or wrinkles, and then incise following the three dimensional folds or wrinkles. The figures are therefore intended to be explanatory and not limiting in any way.

All patents and patent applications cited herein are hereby incorporated by reference in their entirety.

The use of the terms "a" and "an" and "the" and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the embodiments unless otherwise claimed. No language in the specification should be construed as indicating any non-claimed element as essential to the practice of the embodiments.

While certain illustrated embodiments of this disclosure have been shown and described in an exemplary form with a certain degree of particularity, those skilled in the art will understand that the embodiments are provided by way of example only, and that various variations can be made without departing from the spirit or scope of the embodiments. Thus, it is intended that this disclosure cover all modifications, alternative constructions, changes, substitutions, variations, as well as the combinations and arrangements of parts, structures, and steps that come within the spirit and scope of the embodiments as generally expressed by the following claims and their equivalents.

What is claimed is:

1. A method for the precise incision of tissue in a cornea, comprising:
   docking a femtosecond laser patient interface to a cornea of a patient;
   attenuating the femtosecond laser power to a level for measuring,
      wherein the attenuated femtosecond laser has a power at the focus point of less than 40 milliwatts;
   focusing the femtosecond laser to a beam at a focal point in the interior side of the cornea of the patient in x lateral axis, y lateral axis and a z depth axis;
   moving the femtosecond laser focal point in the z axis from the interior side of the cornea through the cornea and toward an exterior side of the cornea;
   capturing a backscatter of the femtosecond laser focal point as it moves in the z axis from the interior side of the cornea to the exterior side of the cornea; and
   recording a time the femtosecond laser focal point moves in the z depth axis from the interior side of the cornea to the exterior side of the cornea;
   calculating a power of the captured backscatter as the laser focal point moves in the z depth axis from the interior side of the cornea to the exterior side of the cornea;
   determining a cutting distance, based on the recorded time the laser focal point moves and the calculated power of the captured backscatter;
   powering up the femtosecond laser from the measuring power to an incision power; and
   incising the cornea at the determined cutting distance in the cornea to remove a portion of the cornea.

2. The method of claim 1 wherein the cutting distance is 50 μm from an endothelium layer of the cornea.

3. The method of claim 1 further comprising,
   determining, from the captured backscatter, a folded shape of the cornea while the patient interface is docked;
   wherein the incision on the cornea at the determined cutting distance follows the folded shape of the docked cornea.

4. The method of claim 3 wherein the incision following the folded shape of the cornea while docked does not incise an endothelium layer in the cornea.

5. The method of claim 1 wherein the laser has a wavelength between 1020 and 1040 nm.

6. The method of claim 1 wherein the laser has a wavelength between 335 and 400 nm.

7. The method of claim 1 wherein the laser beam has a numerical aperture NA between 0.3 and 1.3.

8. The method of claim 1 wherein the laser beam is polarized.

9. The method of claim 1 wherein the laser beam is a pulsed laser beam having a pulse duration between 10 femtoseconds and 10 picoseconds.

10. An ophthalmic surgical laser system comprising:
    a laser system configured to deliver a pulsed laser beam at a focal point, the pulsed laser beam attenuated to,
       a measuring wavelength between 300 nm and 1200 nm, and
       a measuring power at the focal point below 40 milliwatts;
    an xy-scan device configured to move the pulsed laser beam in lateral directions;
    a z-scan device configured to move a depth of focus of the pulsed laser beam; and
    a controller operably coupled with the laser system, the xy-scan device and the z-scan device, the controller configured to direct the laser system to output the pulsed laser beam at various z depths of a cornea starting at an interior of the cornea and moving toward an exterior of the cornea;
    a backscatter capture device configured to,
       capture backscatter from the laser;
       calculate a power of the captured backscatter as the laser focal point moves in the z depth from the interior side of the cornea to the exterior side of the cornea;
       record a time as the laser focal point moves in the z depth;
    a computer configured to determine a cutting distance based on the recorded time the laser focal point moves and the calculated power of the captured backscatter.

11. The system of claim 10 wherein the laser is further configured to,
    deliver a pulsed laser beam at a focal point, the pulsed laser beam attenuated to a cutting wavelength and a cutting power; and
    incise the cornea at the determined cutting distance in the cornea.

12. The system of claim 10 wherein the cutting distance is 50 μm from an endothelium layer of the cornea.

13. The system of claim 11 wherein the computer is further configured to,
    determine, from the captured backscatter, a folded shape of the cornea while the patient interface is docked;
    wherein the incision on the cornea at the determined cutting distance follows the folded shape of the docked cornea.

14. The system of claim 13 wherein the incision following the folded shape of the cornea while docked does not incise an endothelium layer in the cornea.

15. The system of claim 10 wherein the laser has a wavelength between 335 nm and 400 nm.

16. The system of claim 10 wherein the laser system is configured to produce the pulsed laser beam having a numerical aperture NA between 0.3 and 1.3.

17. The system of claim 10 wherein the pulsed laser beam is polarized.

18. The system of claim 10 wherein the laser is configured to produce the pulsed laser beam having a pulse duration between 10 femtoseconds and 10 picoseconds.

19. The system of claim 13 wherein the system is further configured to plot the determined distances on a map corresponding to the laser focus in the x lateral axis and y lateral axis.

20. A method, comprising:
docking a patient eye to a laser treatment system;
in the laser treatment system,
   generating a femtosecond pulsed laser beam of less than 40 milliwatts in power;
   directing the laser beam into the cornea of an eye of a patient, the cornea having an interior side toward a center of the eye and an exterior side;
   focusing the directed laser beam to a focus point beyond the cornea interior into the eye;
   moving the focus point of the laser beam through the cornea toward the exterior side of the cornea;
   moving the focus point of the laser beam past the exterior side of the cornea;
   receiving a backscatter of the laser beam as the focus point moves;
   determining a time corresponding to the received backscatter of the laser beam as the focus point moves;
   calculating a cutting distance from the cornea interior based on the received backscatter and corresponding time as the focus point moves;
   generating a femtosecond pulsed laser beam of greater than 40 milliwatts in power;
   incising the cornea at the calculated cutting distance from the cornea interior;
      wherein the incision on the cornea at the calculated cutting distance follows a folded shape of the docked cornea.

* * * * *